US011623903B2

(12) United States Patent
Marshall et al.

(10) Patent No.: US 11,623,903 B2
(45) Date of Patent: Apr. 11, 2023

(54) ALKANE DEHYDROGENATION CATALYST AND METHODS OF CONVERTING ALKANES TO ALKENES

(71) Applicants: UCHICAGO ARGONNE, LLC, Chicago, IL (US); FORGE NANO, Louisville, CO (US)

(72) Inventors: Christopher L. Marshall, Naperville, IL (US); Zheng Lu, Bolingbrook, IL (US); Jeffrey W. Elam, Elmhurst, IL (US); Christopher Nicholas, Evanston, IL (US); Paul T. Barger, Arlington Heights, IL (US); Martha Leigh Abrams, Chicago, IL (US); Arrelaine Dameron, Boulder, CO (US); Ryon W. Tracy, Westminster, CO (US)

(73) Assignees: UCHICAGO ARGONNE, LLC, Chicago, IL (US); FORGE NANO, Louisville, CO (US)

( * ) Notice: Subject to any disclaimer, the term of this patent is extended or adjusted under 35 U.S.C. 154(b) by 0 days.

(21) Appl. No.: 17/197,997

(22) Filed: Mar. 10, 2021

(65) Prior Publication Data

US 2021/0292258 A1 Sep. 23, 2021

Related U.S. Application Data

(60) Provisional application No. 62/987,841, filed on Mar. 10, 2020.

(51) Int. Cl.
*C07C 5/333* (2006.01)
*B01J 23/42* (2006.01)
(Continued)

(52) U.S. Cl.
CPC ............. *C07C 5/3337* (2013.01); *B01J 21/04* (2013.01); *B01J 21/063* (2013.01); *B01J 23/42* (2013.01); *B01J 23/70* (2013.01); *B01J 33/00* (2013.01); *B01J 35/0006* (2013.01); *B01J 35/023* (2013.01); *B01J 35/1014* (2013.01); *B01J 35/1019* (2013.01); *B01J 35/1038* (2013.01); *B01J 35/1042* (2013.01); *B01J 35/1061* (2013.01); *B01J 37/0207* (2013.01); *B01J 37/0238* (2013.01); *B01J 37/0244* (2013.01);
(Continued)

(58) Field of Classification Search
None
See application file for complete search history.

(56) References Cited

U.S. PATENT DOCUMENTS 2,021,025 A * 11/1935 Saftlas ................ A41D 25/001
2/147
9,284,643 B2 3/2016 King et al.
(Continued)

OTHER PUBLICATIONS

Hocking et al., "Handbook of chemical technology and pollution control". 2nd ed.; Academic Press: San Diego, 1998; p. xxiv, p. 777.
(Continued)

*Primary Examiner* — Ali Z Fadhel
(74) *Attorney, Agent, or Firm* — Marshall, Gerstein & Borun LLP

(57) ABSTRACT

Provided herein is an alkane dehydrogenation catalyst, a method of manufacturing an alkane dehydrogenation catalyst, and a method of converting alkanes to alkenes.

14 Claims, 25 Drawing Sheets

(51) Int. Cl.

| | |
|---|---|
| *B01J 21/06* | (2006.01) |
| *B01J 37/08* | (2006.01) |
| *B01J 37/02* | (2006.01) |
| *B01J 37/18* | (2006.01) |
| *B01J 37/12* | (2006.01) |
| *B01J 35/10* | (2006.01) |
| *B01J 35/02* | (2006.01) |
| *B01J 35/00* | (2006.01) |
| *B01J 21/04* | (2006.01) |
| *B01J 33/00* | (2006.01) |
| *B01J 23/70* | (2006.01) |

(52) U.S. Cl.
CPC ............ *B01J 37/082* (2013.01); *B01J 37/12* (2013.01); *B01J 37/18* (2013.01); *C07C 2521/04* (2013.01); *C07C 2521/06* (2013.01); *C07C 2523/42* (2013.01)

(56) References Cited

U.S. PATENT DOCUMENTS

| | | | |
|---|---|---|---|
| 9,403,150 | B2 | 8/2016 | Lu et al. |
| 9,546,424 | B2 | 1/2017 | King et al. |
| 9,649,627 | B1* | 5/2017 | Xiao .............. B01J 37/0221 |
| 2014/0256966 | A1* | 9/2014 | Dumesic .......... B01J 37/0221 502/343 |
| 2016/0074833 | A1* | 3/2016 | O'Brien ............ B01J 21/06 204/157.52 |
| 2016/0136632 | A1* | 5/2016 | Monnier ............ B01J 37/08 502/313 |
| 2017/0333878 | A1* | 11/2017 | Stair ............. B01J 37/0244 |
| 2018/0147572 | A1* | 5/2018 | Fukumura ........ B01J 20/3204 |
| 2018/0185688 | A1* | 7/2018 | Shaban ............... A62D 3/34 |
| 2019/0249301 | A1* | 8/2019 | Prinz ............... B01J 23/42 |
| 2019/0345090 | A1* | 11/2019 | Vardon ............. B01J 21/04 |
| 2020/0061598 | A1* | 2/2020 | Vardon ............. B01J 35/023 |
| 2020/0168300 | A1* | 5/2020 | Goddard, III ...... B01J 35/0046 |
| 2020/0276569 | A1* | 9/2020 | Hong .............. B01J 37/0217 |
| 2020/0298221 | A1* | 9/2020 | Oh .................. H01M 4/8657 |
| 2021/0060538 | A1* | 3/2021 | Fushimi ............ B01J 27/22 |
| 2021/0252486 | A1* | 8/2021 | Liang ............. B01J 23/38 |
| 2021/0387166 | A1* | 12/2021 | An .................. C07C 45/33 |
| 2021/0408555 | A1* | 12/2021 | Steinbach .......... B01J 35/002 |

OTHER PUBLICATIONS

Economic Plant "Component, Polypropylene," increasing global demand for on-purpose production of propylene, Https://www.economic-plant.com/component/tags/tag/polypropylene.html.

Bricker, "Advanced Catalytic Dehydrogenation Technologies for Production of Olefins". Top Catal 2012, 55 (19-20), 1309-1314.

Siirola J. "The Impact of Shale Gas in the Chemical Industry". Aiche Journal 2014, 60 (3), 810-819.

Vora V.B, "Development of Dehydrogenation Catalysts and Processes". Top Catal 2012, 55 (19-20), 1297-1308.

Sattler et al., "Catalytic Dehydrogenation of Light Alkanes on Metals and Metal Oxides". Chemical Reviews 2014, 114 (20), 10613-10653.

Nawaz, Z., Light alkane dehydrogenation to light olefin technologies: a comprehensive review. Rev Chem Eng 2015, 31 (5), 413-436.

Nicholas et al., "Elucidation of phosphorus interaction in dual component zeolite/matrix catalysts: Selectivity control in olefin oligomerization with MTW/Al2O3". Appl Catal a-Gen 2017, 536, 75-84.

Mitchell et al., From powder to technical body: the undervalued science of catalyst scale up. Chem Soc Rev 2013, 42 (14), 6094-6112.

Zhang et al., "Atomic Layer Deposition Overcoating: Tuning Catalyst Selectivity for Biomass Conversion" Angew Chem Int Edit 2014, 53 (45), 12132-12136.

Lu et al., "Synthesis and Stabilization of Supported Metal Catalysts by Atomic Layer Deposition. Accounts of Chemical Research" 2013, 46 (8), 1806-1815.

O'Neill et al., "Stabilization of Copper Catalysts for Liquid-Phase Reactions by Atomic Layer Deposition" Angew Chem Int Edit 2013, 52 (51), 13808-13812.

Lu et al., "Coking- and Sintering-Resistant Palladium Catalysts Achieved Through Atomic Layer Deposition" Science 2012, 335 (6073), 1205-1208.

Yang et al., "Enhancement of Copper Catalyst Stability for Catalytic Ozonation in Water Treatment Using ALD Overcoating" Acs Applied Materials & Interfaces 2018, 10 (50), 43323-43326.

Feng et al., "Alumina Over-coating on Pd Nanoparticle Catalysts by Atomic Layer Deposition: Enhanced Stability and Reactivity" Catal Lett 2011, 141 (4), 512-517.

Zhang et al., "Enhancing the stability of copper chromite catalysts for the selective hydrogenation of furfural with ALD overcoating (II)—Comparison between TiO2 and Al2O3 overcoatings". J Catal 2015, 326, 172-181.

King et al., "Atomic layer deposition on particles using a fluidized bed reactor with in situ mass spectrometry". Surf Coat Tech 2007, 201 (22-23), 9163-9171.

Perrichon et al., "Metal dispersion of CeO2—ZrO2 supported platinum catalysts measured by H-2 or CO chemisorption". Appl Catal a-Gen 2004, 260 (1), 1 -8.

Wefers et al., "Oxides and Hydroxides of Aluminum. Alcoa Research Laboratories" 1987, Alcoa technical paper, No. 19, rev.

Lei et al., "Effect of Particle Size and Adsorbates on the L-3, L-2 and L-1 X-ray Absorption Near Edge Structure of Supported Pt Nanoparticles". Top Catal 2011, 54 (5-7), 334-348.

Ott et al., "Al3O3 thin film growth on Si(100) using binary reaction sequence chemistry". Thin Solid Films 1997, 292 (1-2), 135-144.

Aarik et al., Atomic layer deposition of titanium dioxide from TiCl4 and H2O: investigation of growth mechanism. Appl Surf Sci 2001, 172 (1-2), 148-158.

Siddiqi et al., Catalyst performance of novel Pt/Mg(Ga)(Al)O catalysts for alkane dehydrogenation. J Catal 2010, 274 (2), 200-206.

Saerens et al., The Positive Role of Hydrogen on the Dehydrogenation of Propane on Pt(111). Acs Catal. 2017, 7 (11), 7495-7508.

Karwal et al., Tailoring nanopore formation in atomic layer deposited ultrathin films. J Vac Sci Technol A. 2018, 36 (1).

Yoshinobu et al., Lateral displacement by transient mobility in chemisorption of CO on Pt(997). Phys Rev Letters. 2003, 90 (24).

Hayden et al., An Infrared Study of the Adsorption of Co on a Stepped Platinum Surface. Surf Sci 1985, 149 (2-3), 394-406.

* cited by examiner

ALKANE DEHYDROGENATION CATALYST AND METHODS OF CONVERTING ALKANES TO ALKENES

CROSS-REFERENCE TO RELATED APPLICATIONS

The benefit of priority to U.S. Provisional Patent Application No. 62/987,841 filed Mar. 10, 2020 is hereby claimed and the disclosure is incorporated herein in its entirety.

STATEMENT OF GOVERNMENT SUPPORT

This invention was made with under CRADA No. A18085 between Honeywell UOP and UChicago Argonne, LLC, operator of Argonne National Laboratory under Contract No. DE-AC02-06CH11357 awarded by the United States Department of Energy. The government has certain rights in the invention.

BACKGROUND

Light alkenes and propylene, in particular, are regarded as critical building blocks for chemical feed stocks. Propylene is one of the most crucial chemical building block in the industry for the production of chemicals such as polypropylene, acrylonitrile, acrylic acid, and propylene oxide (Hocking et al., *Handbook of chemical technology and pollution control.* 2nd ed.; Academic Press: San Diego, 1998; p xxiv, 777 p). Due to the significant need for products derived from propylene, the current global propylene demand is approximately 90 million metric tons (MMT), and is expected to increase to 130 MMT by 2023 (Sattler et al., *Chemical Reviews* 2014, 114 (20), 10613-10653). Currently, propylene is produced mainly through steam and fluidized catalytic cracking of naphtha, light diesel, and other oil byproducts. However, these two commercial approaches cannot meet future demands for propylene. Recently, increases in shale gas production have resulted in a downward trend in the price of the propane and therefore increased interest in propane dehydrogenation (PDH) as a source of propylene. Among the multiple metals known to catalyze dehydrogenation where catalysts have been industrially commercialized, platinum based catalysts are among the most successful. (Vora, *Top Catal* 2012, 55 (19-20), 1297-1308). Platinum based catalysts/processes are both highly active and very selective to the desired product. However, under the high reaction temperature (>600° C.), sintering of platinum nanoparticles can occur, which lowers the available surface area of the platinum used to catalyze the reaction. With increased sintering, the activity and selectivity to propylene decreases significantly. A technique developed in the field to counteract these effects is frequent regeneration under chlorine atmosphere to re-disperse the platinum nanoparticles.

In addition to propane dehydrogenation (PDH), sintering of supported metal nanoparticles is a major technical issue limiting the lifetime and performance of many commercial heterogeneous catalysts. Consequently, in the field of heterogeneous catalysis there is a tremendous incentive to mitigate sintering and improve catalyst longevity. Most studies in the literature have focused on powders, but for industrial applications, formed bodies such as extrudates are generally utilized. One strategy for synthesizing sinter resistant catalysts employs overcoating a protecting layer to inhibit nanoparticle mobility. However, conventional overcoatings tend to reduce catalytic activity.

SUMMARY

There is a need for improvements to overcoating nanoparticles to mitigate sintering and improve catalyst longevity, particularly at high temperatures, without reducing catalytic activity.

In embodiments, a method of manufacturing an alkane dehydrogenation catalyst comprising a catalyst support, catalytic nanoparticles, and an overcoat, can include: calcining the catalyst support at a temperature in a range of about 500° C. to about 1200° C., wherein after calcining, the calcined catalyst support has a total surface area of 50 $m^2/g$ to 350 $m^2/g$; and immersing the calcined catalyst support in a nanoparticle precursor solution comprising a nanoparticle precursor, under conditions sufficient to impregnate the calcined catalyst support with the nanoparticle precursor and form an impregnated catalyst precursor; calcining the impregnated catalyst precursor under conditions sufficient to convert the nanoparticle precursor impregnated in the impregnated catalyst precursor to catalytic nanoparticles to form a calcined impregnated catalyst precursor, wherein the calcining is done at a temperature in a range of about 150° C. to about 600° C.; depositing by atomic layer deposition (ALD) the overcoat onto the calcined catalyst precursor by contacting the calcined catalyst precursor with an ALD precursor and water at a temperature in a range of about 150° C. to about 300° C., and repeating the depositing step one or more times, thereby forming a catalyst intermediate; annealing the catalyst intermediate in air at a temperature of less than about 600° C. for about 30 minutes to about 2 hours, thereby forming the alkane dehydrogenation catalyst.

In embodiments, an alkane dehydrogenation catalyst, can include: a catalyst support infiltrated with a plurality of catalytic nanoparticles, and; an atomic layer deposition overcoat; wherein the plurality of catalytic nanoparticles have an average size of about 0.6 nm to about 1.2 nm, the atomic layer deposition overcoat has a thickness of about 0.12 nm to about 1.2 nm, the catalyst support has a total surface area of 90 $m^2/g$ to 300 $m^2/g$, a pore volume of 0.8 $cm^3/g$ to 0.4 $cm^3/g$, and an average pore size of 6 nm to 17 nm.

In embodiments, a method of converting an alkane to an alkene, can include: flowing the gaseous reactant mixture over the alkane dehydrogenation catalyst, according to the disclosure, at a temperature in a range of about 400° C. to about 800° C. wherein the gaseous reactant mixture comprises hydrogen gas and an alkane gas, and the alkane gas is converted to an alkene as the gaseous reactant mixture is flowed over the alkane dehydrogenation catalyst.

In embodiments, an ALD coated alkane dehydrogenation catalyst, can include: a catalyst support infiltrated with a plurality of catalytic nanoparticles to form an alkane dehydrogenation catalyst, wherein the catalytic nanoparticles comprise at least one metal selected from group 8 metals, and the catalyst support is an extrudate, and an atomic layer deposition overcoat arranged in contact with a portion of a surface of the catalytic nanoparticles to form the ALD coated alkane dehydrogenation catalyst, wherein the coated alkane dehydrogenation catalysis has a hydrogen chemisorption capacity that is substantially the same as a hydrogen chemisorption capacity of the uncoated alkane dehydrogenation catalyst.

In embodiments, an ALD coated alkane dehydrogenation catalyst, can include: a catalyst support infiltrated with a plurality of catalytic nanoparticles to form an alkane dehydrogenation catalyst, wherein the catalytic nanoparticles comprise at least one metal selected from group 8 metals, and the catalyst support is an extrudate; and an atomic layer deposition overcoat, wherein the atomic layer deposition overcoat is deposited onto the alkane dehydrogenation catalyst by 2-5 cycles of atomic layer deposition when the alkane dehydrogenation catalyst has a surface area of about 80 m$^2$/g to about 100 m$^2$/g or 5-8 cycles of atomic layer deposition when the alkane dehydrogenation catalyst has a surface area of about 80 m$^2$/g to about 100 m$^2$/g.

In embodiments, an ALD coated alkane dehydrogenation catalyst, can include: a catalyst support infiltrated with a plurality of catalytic nanoparticles to form an alkane dehydrogenation catalyst, wherein the catalytic nanoparticles comprise at least one metal selected from group 8 metals, and the catalyst support is an alumina extrudate; and an atomic layer deposition overcoat; wherein the alumina extrudate is in a γ phase, a θ phase, a α phase, or a combination thereof.

BRIEF DESCRIPTION OF FIGURES

FIG. 10 is a STEM image of an alkane dehydrogenation catalyst (0.5 Pt/medium SA) in accordance with embodiments of the disclosure. The inset shows the Pt nanoparticle size distribution;

DETAILED DESCRIPTION

Figure 1A:
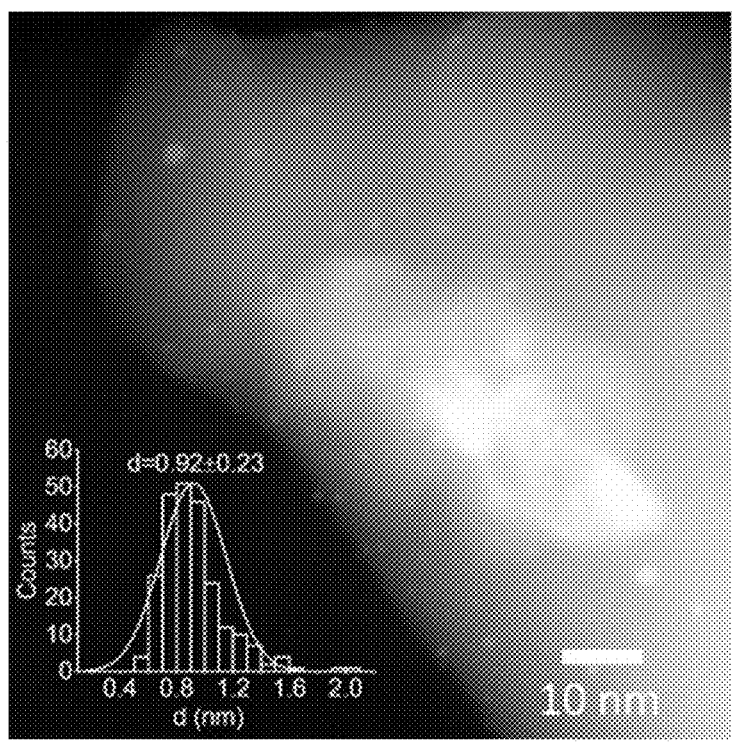
FIG. 1A is a STEM image of an alkane dehydrogenation catalyst (0.1 Pt/ultra-low surface area (SA)) in accordance with embodiments of the disclosure. The inset shows the Pt nanoparticle size distribution.
Figure 1B:
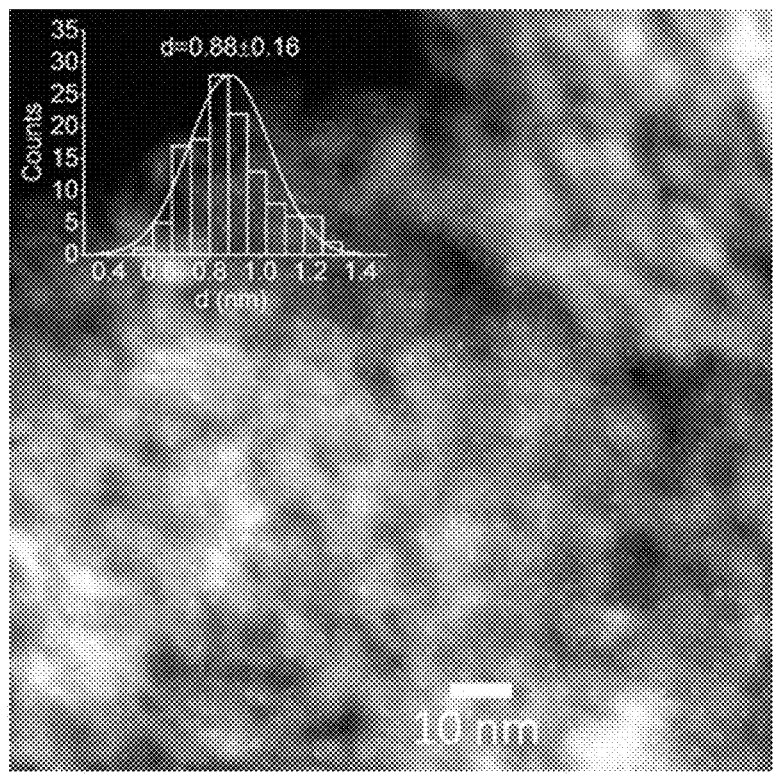
FIG. 1B is a STEM image of an alkane dehydrogenation catalyst (0.5 Pt/ultra-high SA) in accordance with embodiments of the disclosure. The inset shows the Pt nanoparticle size distribution.
Figure 1C:
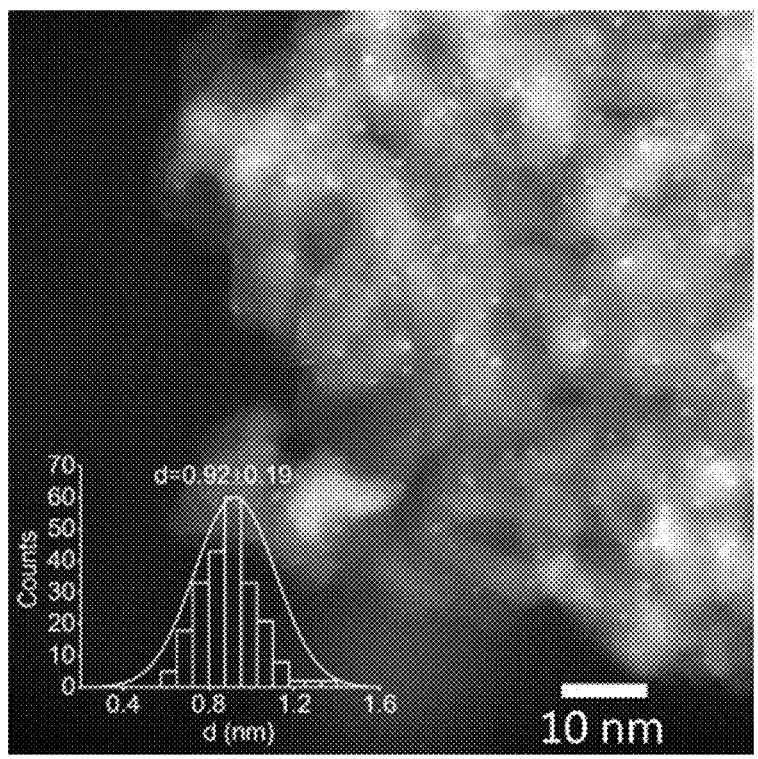
FIG. 1D is a STEM image of an alkane dehydrogenation catalyst (0.5 Pt/ultra-low SA) in accordance with embodiments of the disclosure. The inset shows the Pt nanoparticle size distribution.
Figure 1D:
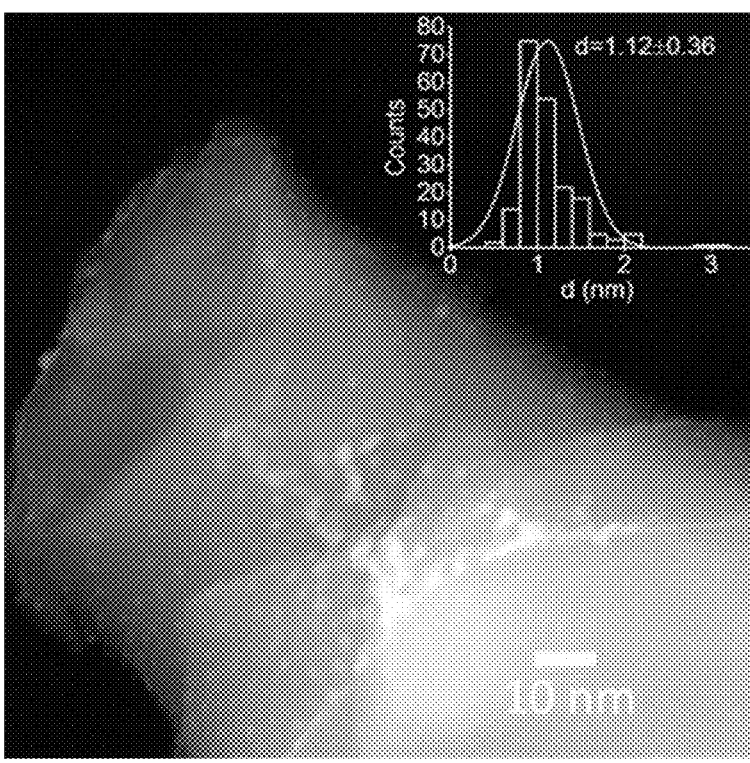

In accordance with embodiments, alkane dehydrogenation catalysts can include a catalyst support infiltrated with a plurality of catalytic nanoparticles and an atomic layer deposition (ALD) overcoat. It has been advantageously found that the alkane dehydrogenation catalysts of the disclosure have improved resistance to sintering, while maintaining good catalytic activity and selectivity towards alkenes. Without intending to be bound by theory, it is believed that the improved performance is, at least in part, due to the presence of a thin ALD overcoat applied to the catalytic nanoparticle and catalyst support. Further, advantageously catalyst in accordance with embodiments of the disclosure can be formed using extrudates as catalysts supports, which can be advantageous over conventional powders.

In embodiments, the alkane dehydrogenation catalyst provided herein can maintain catalytic activity and selectivity towards alkenes after a 1 hour steam treatment at 700° C. In embodiments, the alkane dehydrogenation catalyst provided herein can maintain catalytic activity and selectivity towards alkenes after a 4 hour steam treatment at 700° C. In embodiments, the alkane dehydrogenation catalyst provided herein can maintain catalytic activity and selectivity towards alkenes after 2 or more 1 hour steam treatments at 700° C. In embodiments, the alkane dehydrogenation catalyst provided herein can maintain catalytic activity and selectivity towards alkenes after 5 or more 1 hour steam treatments at 700° C. In embodiments, the alkane dehydrogenation catalyst provided herein can maintain catalytic activity and selectivity towards alkenes after 2 or more 4 hour steam treatments at 700° C. In embodiments, the alkane dehydrogenation catalyst provided herein can maintain catalytic activity and selectivity towards alkenes after 400 or more 4 hour steam treatments at 700° C.

Generally, catalysts having good catalytic activity and/or maintained catalytic activity have an alkane conversion in a range of about 5% to about thermodynamic equilibrium level of alkane conversion. For example, the catalysts of the disclosure can have a catalytic activity before and/or after heat treatments of about 5% to about 50%, or about 5% to about 40%, or about 5% to about 30%.

Generally, catalysts of the disclosure can have and/or maintain, after thermal treatment, an alkene selectivity of about 70% or more, such as about 80% or more, or about 85% or more, or about 90% or more.

Without intending to be bound by theory, it is believed that reduction in catalytic activity of conventional Pt alkane dehydrogenation catalysts was due to sintering of small Pt nanoparticles into large Pt clusters, thereby decreasing the metallic surface area available for reaction.

Catalysts of the disclosure advantageously having an atomic layer deposited overcoat that preferentially deposits on non-catalytic nanoparticle sites, thus providing protection against sintering without reducing the catalytic activity of the active catalytic nanoparticle sites.

As used herein, the term "non-active catalytic nanoparticle sites" refers to nanoparticle sites that have no or substantially no adsorbed $H_2$ when subject to the Chemisorption Test method described in detail below. For example, less than 5%, less than 1%, less than 0.5%, of the total adsorbed $H_2$ as measured by the Chemisorption Test Method can be adsorbed by the non-active catalytic nanoparticle sites.

In accordance with embodiments, a method of manufacturing an alkane dehydrogenation catalyst is provided. In embodiments, the method of manufacturing a coated alkane dehydrogenation catalyst can include performing a hydrogen chemisorption test described herein as the Chemisorption Test Method, at interim stages of the coating and/or at the end of the coating to determine the percent catalytically active sites remaining after coating. This can be useful in determining whether additional coating can be applied, such as through additional ALD cycles as described herein. In embodiments, the coating can be applied until the percent of active sites is about 50% as measured by the Chemisorption Test Method. Other suitable threshold percentages for the amount of active sites are also contemplated herein.

In accordance with embodiments, a method of converting alkanes to alkenes is provided. The method can include an alkane dehydrogenation catalyst and a gaseous reactant. The gaseous reactant mixture can include an alkane. The method of converting alkanes to alkenes can advantageously have an equilibrium conversion of alkanes to alkenes between about 30% to about 40%, a total amount of thermal cracking of the catalyst of less than 3% after 20 hours (e.g., less than 1%), and/or an alkene selectivity of greater than about 85%.

Alkane Dehydrogenation Catalyst

The alkane dehydrogenation catalyst can include a catalyst support infiltrated with a plurality of catalytic nanoparticles and an atomic layer deposition overcoat. In embodiments, the plurality of catalytic nanoparticles have an average size of about 0.6 nm to about 1.2 nm. In embodiments, the atomic layer deposition overcoat has a thickness of about 1.2 Å to about 1.2 nm. In embodiments, the catalyst support has a total surface area of 50 $m^2/g$ to 300 $m^2/g$. In embodiments, the catalyst support has a pore volume of 0.8 $cm^3/g$ to 0.4 $cm^3/g$. In embodiments, the catalyst support has an average pore size of 6 nm to 17 nm. In embodiments, the plurality of catalytic nanoparticles have an average size of about 0.6 nm to about 1.2 nm, the atomic layer deposition overcoat has a thickness of about 0.12 nm to about 1.2 nm, the catalyst support has a total surface area of 50 $m^2/g$ to 300 $m^2/g$, a pore volume of 0.8 $cm^3/g$ to 0.4 $cm^3/g$, and an average pore size of 6 nm to 17 nm.

In any of the embodiments herein, the catalyst support can be an extrudate or other formed bodies known in the art. The extrudates disclosed herein can be porous. In embodiments, the extrudate can include a ceramic and/or metal oxide material, such as alumina. In embodiments, the ceramic and/or metal oxide material can be in one or more different polymorph phases. For example, when the extrudate is alumina, the alumina can be in a γ phase, a θ phase, an α phase, or a combination thereof. In embodiments, each extrudate polymorph phase, independently, has a different surface area corresponding to it. For example, a θ/α phase of an alumina extrudate can have a surface area of about 80 $m^2/g$ to about 100 $m^2/g$, while a γ/θ phase of an alumina extrudate can have a surface area of about 200 $m^2/g$ to about 220 $m^2/g$. In embodiments wherein the extrudate is alumina, the alumina extrudate can be in the θ/α phase and have a surface area of about 80 $m^2/g$ to about 100 $m^2/g$.

In embodiments, the catalyst support can include one or more of alumina ($Al_2O_3$), silica, aluminum phosphate, titania, zirconia, and a combination thereof.

The surface areas and porosities disclosed herein can be and, in embodiments, were measured using nitrogen gas ($N_2$) physisorption by Brunauer-Emmett-Teller (BET) analysis.

The catalyst support can have a total surface area of about 10 $m^2/g$ or more. In embodiments, the catalyst support can have a total surface area of about 10 $m^2/g$ to about 1000 $m^2/g$, about 10 $m^2/g$ to about 500 $m^2/g$, about 50 $m^2/g$ to about 300 $m^2/g$, about 60 $m^2/g$ to about 250 $m^2/g$, about 60 $m^2/g$ to about 200 $m^2/g$, or about 70 $m^2/g$ to about 150 $m^2/g$, or about 80 $m^2/g$ to about 100 $m^2/g$. For example, the catalyst support can have a total surface area of about 50 $m^2/g$, about 60 $m^2/g$, about 70 $m^2/g$, about 75 $m^2/g$, about 80 $m^2/g$, about 85 $m^2/g$, about 90 $m^2/g$, about 95 $m^2/g$, about 100 $m^2/g$, about 105 $m^2/g$, about 110 $m^2/g$, about 120 $m^2/g$, about 130 $m^2/g$, about 140 $m^2/g$, about 150 $m^2/g$, about 200 $m^2/g$, about 210 $m^2/g$, about 250 $m^2/g$, about 280 $m^2/g$, or about 300 $m^2/g$.

In embodiments, maintaining a total surface area of the catalyst support of about 50 $m^2/g$ to about 120 $m^2/g$ was found to require a lower amount of ALD overcoat needed to maintain a high level of stability.

The catalyst support can have a pore volume of about 0.1 $cm^3/g$ or more. In embodiments, the catalyst support can have a pore volume of about 0.1 $cm^3/g$ to about 1 $cm^3/g$, or about 0.2 cm$^3$/g to about 0.9 cm$^3$/g, or about 0.3 cm$^3$/g to about 0.9 cm$^3$/g, or about 0.4 cm$^3$/g to about 0.8 cm$^3$/g, or about 0.5 cm$^3$/g to about 0.8 cm$^3$/g. For example, the catalyst support can have a pore volume of about 0.1 cm$^3$/g, 0.2 cm$^3$/g, 0.3 cm$^3$/g, 0.4 cm$^3$/g, 0.5 cm$^3$/g, 0.6 cm$^3$/g, 0.7 cm$^3$/g, 0.8 cm$^3$/g, 0.9 cm$^3$/g, or 1 cm$^3$/g.

The catalyst support can have an average pore size as determined by $N_2$ physisorption measurements of about 1 nm to about 30 nm. In embodiments, the catalyst support can have an average pore sized of about 5 nm to about 25 nm, about 5 nm to about 20 nm, about 5 nm to about 18 nm, about 6 nm to about 17 nm, or about 7 nm to about 16 nm. For example, the catalyst support can have an average pore size of about 1 nm, 5 nm, 6 nm, 7 nm, 8 nm, 9 nm, 10 nm, 11 nm, 12 nm, 13 nm, 14 nm, 15 nm, 16 nm, 17 nm, 20 nm, 25 nm, or 30 nm.

The plurality of catalytic nanoparticles can include and/or be a transition metal. In embodiments, the plurality of catalytic nanoparticles can include and/or be one or more of platinum, palladium, ruthenium, rhodium, or iridium. In embodiments, the plurality of catalytic nanoparticles can include platinum, palladium, or a combination thereof. In embodiments, the plurality of catalytic nanoparticles can include platinum. The plurality of catalytic nanoparticles have an average size of about 0.1 nm or more. In embodiments, the plurality of catalytic nanoparticles have an average size of about 0.3 nm to about 2 nm, about 0.5 nm to about 1.8 nm, about 0.6 nm to about 1.5 nm, about 0.6 nm to about 1.2 nm, about 0.7 nm to about 1 nm. For example, the average size of the plurality of catalytic nanoparticles can be about 0.1 nm, 0.2 nm, 0.3 nm, 0.4 nm, 0.5 nm, 0.6 nm, 0.7 nm, 0.8 nm, 0.9 nm, 1 nm, 1.1 nm, 1.2 nm, 1.3 nm, 1.5 nm, or about 2 nm.

Atomic layer deposition (ALD) is a thin film deposition technique based on sequential self-limiting surface reactions with gas phase precursors. These reactions take place from gas-phase chemical precursors which are individually and alternately dosed into and removed from a reactor to form no more than monolayer films. In embodiments, the atomic layer deposition overcoat can be deposited by high throughput atomic layer deposition.

Conventional catalyst overcoating with ALD systems often result in dense coatings that hampered or reduced the catalytic activity. This resulted from the use of conventional ALD coating equipment and process parameters, which were designed for coating dense, planar substrates such as the silicon wafers used by the microelectronics industry.

By adjusting the deposition conditions, conventional ALD equipment can be used to coat small quantities of catalyst substrates such as powders and extrudates, in single-gram batches. Although this process is acceptable for bench-scale research, it is time consuming, wasteful of precursor, and impractical to scale for catalyst manufacturing. It has been advantageously found that a high-throughput particle ALD coating process that delivers lean manufacturing approaches can supplant traditional batch ALD reactor systems, for low-cost adoption. The ALD process suitable for use in the methods of the disclosure is further described in Example 7 and FIG. 9, as well as U.S. Pat. Nos. 9,284,643 & 9,546,424, which are incorporated herein in their entirety.

Although any sequence is feasible, in embodiments, the ALD reactions herein can include an A/B/A/B sequence or an A/B/C/A/B/C sequence, wherein A and B are different ALD precursors, and A, B, and C are different ALD precursors. ALD allows for precise thickness control and conformal deposition on highly porous substrates. In embodiments wherein the ALD reaction includes an A/B sequence, the ALD precursors can include for A: Al, Ti, Nb, Zr, and V; and for B: water, hydrogen peroxide or the like. In embodiments, the ALD precursor: A can include trimethylaluminum, diethyl zinc, titanium tetraisopropoxide, titanium tetrachloride, or the like.

In embodiments, the calcined catalyst precursors can be loaded into an ALD reactor and heated to a temperature in a range of about 200° C. to about 500° C. (e.g., about 300° C.) for about 1 hour to about 12 hours. In an embodiment, the temperature can be about 300° C., with a heating time of about 2 hours. In embodiments, said process can take place under vacuum to remove adventitious moisture from the system. In embodiments, the catalyst precursors loaded in the ALD reactor at a temperature in a range of about 200° C. to about 500° C. can be cooled to a lower temperature, for example, about 300° C. to about 200° C.). In embodiments, an inert gas (for example, $N_2$) can be flowed through the reactor for the duration of the experiment to act as a carrier gas for the reaction. In embodiments, the ALD reaction can include an A/B sequence, such as trimethylaluminum and water as the ALD precursors. In embodiments, wherein trimethylaluminum and water are used as ALD precursors, an aluminum oxide film can be formed with methane forming as the reaction by-product. Different numbers of ALD precursor (e.g., TMA and water) "cycles", the process of dosing each ALD precursor once to form a monolayer film, can be completed to form the ALD overcoat (e.g., aluminum oxide layers) of varying thickness on the calcined catalyst precursor. The reactor can then be cooled to room temperature and the coated catalyst (catalyst intermediate) can be unloaded. The catalyst intermediate can then be stored in dry boxes to limit moisture uptake during storage.

The atomic layer deposition overcoat can include one or more of Al, Ti, Nb, Zr, and V. In embodiments, the atomic layer deposition overcoat can include one or more of $Al_2O_3$, $TiO_2$, $ZrO_2$, $Nb_2O_5$, and $V_2O_5$. In embodiments, the atomic layer deposition overcoat can include one or more of $Al_2O_3$, $TiO_2$, and $ZrO_2$. In embodiments, the atomic layer deposition overcoat can comprise $Al_2O_3$.

The atomic layer deposition overcoat can have a thickness of about 1 Å or more. In embodiments, the atomic layer deposition overcoat can have a thickness of about 1 Å to about 10 nm, or about 1 Å to about 5 nm, or about 1 Å to about 2 nm, or about 1 Å to about 1.2 nm, or about 1.2 Å to about 1 nm, or 1.2 Å to about 0.8 nm, or about 5 Å to about 1.2 nm or about 5 Å to about 1.1 nm. For example, the atomic layer deposition overcoat can have a thickness of about 1 Å, 1.1 Å, 1.2 Å, 1.3 Å, 1.5 Å, 2 Å, 3 Å, 4 Å, 5 Å, 6 Å, 7 Å, 8 Å, 9 Å, 10 Å, 1.1 nm, 1.2 nm, 1.5 nm, 2 nm, or 5 nm. In embodiments, the overcoat can have thickness of less than 5 nm.

It can be advantageous to have an ALD overcoat as described herein to improve the catalytic nanoparticles stability (e.g., resistance to sintering). It has been found, however, an ALD overcoat can decrease catalytic nanoparticle activity towards alkenes if it is too thick. It has been found that over coat thickness of less than 5 nm can provide improved stability without reduction of the catalytic activity.

The ALD overcoat can cover approximately about 5% or more of the total surface area of the catalytic nanoparticles. In embodiments, the ALD overcoat can cover approximately about 5% to about 80%, or about 10% to about 70%, or about 10% to about 60%, or about 20% to about 60%, or about 30% to 60%. For example, the ALD overcoat can cover approximately about 5%, 10%, 20%, 30%, 40%, 50%, 60%, 70%, or 80%.

In embodiments, the alkane dehydrogenation catalyst can include about 0.05 wt % nanoparticles to about 0.6 wt % nanoparticle, based on the total weight of the alkane dehydrogenation catalyst. In embodiments, the alkane dehydrogenation catalyst can include about 0.05 wt %, 0.06 wt %, 0.07 wt %, 0.08 wt %, 0.09 wt %, 0.1 wt %, 0.2 wt %, 0.3 wt %, 0.4 wt %, 0.5 wt %, or 0.6 wt %, based on the total weight of the alkane dehydrogenation catalyst.

In embodiments, the alkane dehydrogenation catalyst can have about 50% to about 90% of active metal nanoparticle sites, as measured by the Chemisorption Test Method. In embodiments, the alkane dehydrogenation catalyst can have about 50% to 90%, about 60% to about 85%, or about 70% to about 85%, or about 55% to about 80%, or about 40% to about 80%, or about 50% to about 60%, of active metal nanoparticle sites, as measured by the Chemisorption Test Method. For example, the alkane dehydrogenation catalyst can have about 50%, 55%, 60%, 65%, 70%, 75%, 80%, 85%, 90%, or 95%, of active metal nanoparticle sites, as measured by the Chemisorption Test Method.

In embodiments, the alkane dehydrogenation catalyst has improved stability, for example, as demonstrated by the presence of about 50% to about 90% active metal nanoparticle sites after annealing for 1 hour at 500° C., as measured by the Chemisorption Test Method. The steam treatment, described further in the Examples herein, is used to simulate the long-term effects (weeks/months) on the alkane dehydrogenation catalyst under commercial reaction conditions. In embodiments, the alkane dehydrogenation catalyst can have at least 50%, at least 60%, at least 70%, or at least 80% active metal nanoparticle sites after annealing for 1 hour at 500° C., as measured by the Chemisorption Test Method.

In embodiments, the catalytic nanoparticles include at least one metal selected from group 8 metals.

In embodiments, the alkane dehydrogenation catalyst of the disclosure having an ALD overcoat can have a hydrogen chemisorption capacity that is within 20% of the hydrogen chemisorption capacity of an uncoated alkane dehydrogenation catalyst. In embodiments, the alkane dehydrogenation catalyst of the disclosure having an ALD overcoat, has a hydrogen chemisorption capacity that is within 10% or within 20% of the hydrogen chemisorption capacity of an uncoated alkane dehydrogenation catalyst as determined by the Chemisorption Test Method described in detail below. In embodiments, the alkane dehydrogenation catalyst of the disclosure having an ALD overcoat has a hydrogen chemisorption capacity that is within 5% of the hydrogen chemisorption capacity of an uncoated alkane dehydrogenation catalyst.

In embodiments, the ALD coated alkane dehydrogenation catalyst can include a catalyst support infiltrated with a plurality of catalytic nanoparticles to form an alkane dehydrogenation catalyst, wherein the catalytic nanoparticles comprise at least one metal selected from group 8 metals, and the catalyst support is an extrudate, and an atomic layer deposition overcoat comprising $Al_2O_3$.

In embodiments, the atomic layer deposition overcoat is deposited onto the alkane dehydrogenation catalyst by 2-5 cycles of atomic layer deposition when the alkane dehydrogenation catalyst has a surface area of 80 $m^2/g$ to 100 $m^2/g$ or 5-8 cycles of atomic layer deposition when the alkane dehydrogenation catalyst has a surface area of 80 $m^2/g$ to 100 $m^2/g$.

In embodiments, the ALD coated alkane dehydrogenation catalyst can include a catalyst support infiltrated with a plurality of catalytic nanoparticles to form an alkane dehydrogenation catalyst, wherein the catalytic nanoparticles can include at least one metal selected from group 8 metals, and the catalyst support is an alumina extrudate; and an atomic layer deposition overcoat; wherein the alumina extrudate is in a γ phase, a Θ phase, a α phase, or a combination thereof.

Methods of Preparing an Alkane Dehydrogenation Catalyst

In accordance with embodiments, a method of manufacturing an alkane dehydrogenation catalyst is provided. The alkane dehydrogenation catalyst can include a catalyst support, catalytic nanoparticles, and an overcoat, and can have any of the attributes and features as described above for any of the embodiments herein. In embodiments, the catalyst support can be an extrudate.

The method of manufacturing an alkane dehydrogenation catalyst can include calcining the catalyst support, immersing the calcined catalyst support in a nanoparticle solution thereby forming a catalyst precursor impregnated with the nanoparticle precursor, calcining the impregnated catalyst precursor under conditions sufficient to convert the nanoparticle precursor impregnated in the catalyst precursor to catalytic nanoparticles, depositing by atomic layer deposition (ALD) the overcoat onto the calcined catalyst precursor by contacting the calcined catalyst precursor with an ALD precursor and water, and repeating the depositing step one or more times, thereby forming a catalyst intermediate, and annealing the catalyst intermediate in air, thereby forming the alkane dehydrogenation catalyst.

In embodiments, the method can include determining a percentage of active catalytic sites by testing the $H_2$ chemisorption using the Chemisorption Test Method after a first ALD deposition of the overcoat before repeating the depositing step one or more times. The depositing step can be repeated if the percent catalytically active sites is at least about 50% as measured by the Chemisorption Test Method. The depositing step can be repeated, with intervening testing of the percent of catalytically active sites between deposition cycles. This can ensure a sufficient number of catalytically active sites remain, while maximizing the coating that can be applied. This can also allow the method of the disclosure to be tailored to different catalytic supports and catalytically particles, which may react differently in terms of the number of active sites remaining after the ALD coating process. For example, as show in Example 6, low surface area materials were found to allow for increased number of ALD cycles while maintaining a suitable number of active sites for the catalytic purposes. Intermittent testing of the percent active sites using the Chemisorption Test Method can advantageously allow one to determine the precise number of ALD coating cycles that result in a desired catalyst, balancing catalytic activity against the thickness of the ALD coating and thereby the amount of stability afforded against sintering. The catalyst can be tested any number of times during the coating cycle, for example, after each cycle, after 2 or more cycles, or after any suitable number of cycles. Testing can be done at different increments of the coating cycles, as well. For example, a first testing can be performed after a two or more cycles are performed and then repeated between each subsequent cycle. In embodiments, the deposition can be repeated until at least about 90%, 80%, 70%, 60%, or 50% of the catalytically active sites remain as measured by the Chemisorption Test Method. Any suitable threshold value of catalytically active sites can be selected depending on the catalyst being formed and desired applications. The methods of the disclosure advantageously allow for such tailoring of the ultimate catalytic activity and stability.

In embodiments, methods of the disclosure can utilize the Chemisorption Test Method to validate catalytic activity during production, for example, during commercial production, by selectively testing the coated catalysts from batches of the production.

In embodiments, method of the disclosure can utilize the Chemisorption Test Method in determining a suitable number of ALD coating cycles that can be performed while obtaining a desired threshold value of the active sites. In such embodiments, the Chemisorption Test Method can be used intermittently between coating cycles. In embodiments, the method can include performing ALD coating cycles until the threshold value of active sites is failed, as measured by the Chemisorption Test Method. This can help to identify the maximum number of coating cycles that can be performed while meeting the threshold hold active sites. The coating cycle determination made in such a method can then be used for a larger-scale production of the catalyst. As noted above, even during such larger-scale production, the Chemisorption Test Method can be used on selected catalysts from batches as a validation that the method is resulting in catalyst with desired active sites and that consistent results are being achieved.

In embodiments, the catalyst support can be calcined at a temperature of about 500° C. to about 1200° C., or about 500° C. to about 1050° C., or about 600° C. to about 1050° C., or about 500° C. to about 800° C., or about 600° C. to about 800° C., or about 750° C. to about 1050° C. In embodiments, the temperature can be about 500° C., 600° C., 750° C., 1050° C., 1100° C., 1150° C., or 1200° C.

In embodiments, the catalyst support can be calcined for about 1 hour or more. For example, the catalyst support can be calcined for about 2 hours, 3 hours, 4 hours, 5 hours, 8 hours, 10 hours, 12 hours, 15 hours, 20 hours, or 24 hours.

In embodiments, after calcining the catalyst support, the calcined catalyst support can have a total surface area of 50 $m^2/g$ to 350 $m^2/g$. In embodiments, after calcining the catalyst support, the calcined catalyst support can have a total surface area of 50 $m^2/g$ to 350 $m^2/g$, a pore volume of 0.8 $cm^3/g$ to 0.4 $cm^3/g$, and an average pore size of 3 nm to 20 nm as determined by Hg porosimetry.

Calcining of the catalyst support can advantageously provide changes in the surface area, pore volume, and pore size of the catalyst support, in turn, this can allow for the alkane dehydrogenation catalyst to be tailored for high catalytic activity and selectivity, as well as high resistance to sintering and overall longevity of the alkane dehydrogenation catalyst.

The calcined catalyst support can be immersed in a nanoparticle precursor solution comprising a nanoparticle precursor. The nanoparticle precursor solution can include the nanoparticle precursor and water or other suitable solvent. In embodiments, the nanoparticle precursor solution can include the nanoparticle precursor dissolved in water. In embodiments, nanoparticle precursor is present in the nanoparticle precursor solution at a concentration of about 0.01 M to about 6 M, or about 0.1 M to about 3 M, or about 0.1 M to 1 M, or about 0.5 M to 2.5 M, or about 1 M to about 2 M. For example, the nanoparticle precursor is present in the nanoparticle precursor solution at a concentration of about 0.01 M, 0.1 M, 0.5 M, 1 M, 1.5 M, 2 M, 2.5 M, 3 M, 4 M, 5 M, or 6 M.

The nanoparticle precursor as disclosed herein can include one or more group 8 transition metals. In embodiments, the nanoparticle precursor can include one or more of $H_2PtCl_6$, chloroplatinic acid, ammonium chloroplatinate, bromoplatinic acid, platinum trichloride, platinum tetrachloride hydrate, platinum dichlorocarbonyl dichloride, tetraamineplatinum chloride, dinitrodiaminoplatinum, and sodium tetranitroplatinate (II). In embodiments, the nanoparticle precursor is or includes $H_2PtCl_6$.

After immersion in the nanoparticle precursor solution, the impregnated catalyst precursor is again calcined, and can be calcined under conditions sufficient to convert the nanoparticle precursor impregnated in the impregnated catalyst precursor to catalytic nanoparticles to form a calcined catalyst precursor. For example, the calcining of the impregnated catalyst precursor can be done at a temperature in a range of about 500° C. to about 1200° C. In embodiments, the temperature can be about 500° C. to about 1200° C., or about 500° C. to about 1050° C., or about 600° C. to about 1050° C., or about 500° C. to about 800° C., or about 750° C. to about 1050° C. In embodiments, the temperature can be about 500° C., 600° C., 750° C., 1050° C., or 1200° C. In embodiments, the impregnated catalyst precursor can be calcined for about 10 minutes or more. For example, the impregnated catalyst precursor can be calcined for about 10 minutes, 30 minutes, 1 hour, 2 hours, 3 hours, 4 hours, 5 hours, 8 hours, 10 hours, 12 hours, 15 hours, 20 hours, or 24 hours. In embodiments, the catalyst precursor can be calcined for about 0.5 hours to 3 hours. Suitable times and temperatures can be selected and tailored based on the nanoparticle precursor material.

The ALD overcoat can be deposited through atomic layer deposition onto the calcined impregnated catalyst precursor using an ALD precursor and water. Deposition of the ALD overcoat can be done at a temperature in a range of about 125° C. to about 500° C., or about 150° C. to about 300° C., or about 175° C. to about 275° C., or about 175° C. to about 250° C. For example, the deposition of the ALD overcoat can be done at a temperature of 125° C., 150° C., 175° C., 200° C., 225° C., 250° C., 275° C., 300° C., 400° C., or 500° C.

In embodiments, the overcoat can be deposited onto the calcined impregnated catalyst precursor under vacuum.

In embodiments, the ALD precursor can include one or more of Al, Ti, Nb, Zr, and V. Reference herein will be made to a "ALD precursor" and should be understood to include embodiments of a single gas as well as embodiments of a mixture of gasses. In embodiments, the ALD precursor can include one or more of $Al(CH_3)_3$, $TiCl_4$, $ZrCl_4$, $Zr(N(CH_3)_2)_4$, $Nb(OCH_2CH_3)_5$, and $V(O)(OCH(CH_3)_2)_3$. In embodiments, the ALD precursor is TMA.

The depositing step can be repeated one or more times, thereby forming a catalyst intermediate. In embodiments, the depositing step can be repeated 2 to 200 times, or 2 to 100 times, or 2 to 50 times, or 2 to 20 times, or 2 to 10 times, or 2 to 8 times, or 3 to 6 times. For example, the depositing step can be repeated 2, 3, 4, 5, 6, 7, 8, 9, 10, 15, 20, 25, 30, 50, 100, or 200 times. In embodiments, the growth rate of the ALD overcoat can be about 0.1 nm to 0.14 nm per ALD cycle (depositing step). It has been found that depositing the ALD overcoat onto the calcined impregnated catalyst precursor can be advantageous when the depositing step is repeated 2 to 8 times, or 3 to 6 times, as the catalytic nanoparticles are then both resistant to sintering and maintain good catalytically active. The thickness of the ALD overcoat is advantageous when it is about 0.2 nm to about 1.3 nm, as the catalytic nanoparticles are then both resistant to sintering and catalytically active.

Depositing an atomic layer overcoat by ALD on porous supports, such as the extrudates disclosed herein, can be more complicated than depositing an ALD overcoat on a traditional planar support. The diffusion of the precursors and products into and out of the high-aspect-ratio pores can be slow. Advantageously, the methods disclosed herein can deposit an atomic layer overcoat by ALD on porous supports, such as extrudates, without altering the size of the nanoparticles.

Further, the catalyst intermediate can be annealed. Annealing the catalyst intermediate can take place in open air at a temperature of less than about 600° C. for a period of time, thereby forming the alkane dehydrogenation catalyst. In embodiments, the temperature can be less than about 550° C., or about 450° C. to 600° C., or about 450° C. to 550° C. For example, the catalyst intermediate can be annealed at a temperature of about 500° C. In embodiments, the catalyst intermediate can be annealed for about 15 minutes to about 6 hours, or about 30 minutes to about 3 hours, or about 30 minutes to 2 hours, or about 30 minutes to 1.5 hours. For example, the catalyst intermediate can be annealed for about 1 hour.

Method of Converting Alkane to Alkene.

Further provided herein is a method of converting an alkane to an alkene using the catalyst of the disclosure. The method of converting an alkane to an alkene can include flowing a gaseous reactant mixture over the alkane dehydrogenation catalyst. The gaseous reactant mixture can include alkane gas and optionally, hydrogen gas, wherein the alkane gas is converted to an alkene as the gaseous reactant mixture is flowed over the alkane dehydrogenation catalyst. In embodiments, the temperature can be in a range of about 400° C. to about 800° C.

In embodiments, the gaseous reactant mixture can include an alkane gas. In some embodiments, the alkane gas can include one or more of ethane, propane, butane (e.g., isobutane), pentane, hexane, heptane, octane, nonane, and further higher alkanes. The alkane gases as used herein can be straight chained or branched alkanes. In embodiments, the alkane gas can be one or more of ethane, propane, and butane (e.g., isobutane). In some embodiments, the alkane is propane and/or isobutane. In embodiments, the gaseous reactant mixture can include hydrogen gas. In embodiments the gaseous reactant mixture can include hydrogen gas, the ratio of hydrogen gas to alkane gas can be about 5:1 to about 1:100, based on volume %, or about 2:1 to about 1:10, or about 1:1 to about 1:10, or about 1:2 to about 1:10. For examples, the ratio of hydrogen gas to alkane gas can be 5:1, 3:1, 2:1, 1:1, 1:2, 1:3, 1:4, 1:5, 1:10, or 1:100.

The alkane gas is converted to an alkene as the gaseous reactant mixture is flowed over the alkane dehydrogenation catalyst. In embodiments, the alkene can be one or more of ethylene, propylene, butylene (e.g., isobutylene), pentene, hexene, heptene, octene, nonene, and further higher alkenes. In embodiments, the alkene can be one or more of ethene, propene, and butene. In some embodiments, the alkene is propene and/or isobutylene. In embodiments, the propane gas is converted to propylene or the isobutane gas is converted to isobutylene, as the gaseous reactant mixture is flowed over the alkane dehydrogenation catalyst.

The gaseous reactant mixture is flowed over the alkane dehydrogenation catalyst at any suitable space velocity. In embodiments, the space velocity can be about 10,000 $h^{-1}$ to about 700,000 $h^{-1}$, or about 30,000 $h^{-1}$ to about 650,000 $h^{-1}$, or about 50,000 $h^{-1}$ to about 600,000 $h^{-1}$, or about 60,000 $h^{-1}$ to about 600,000 $h^{-1}$, or about 60,000 $h^{-1}$ to about 120,000 $h^{-1}$, or about 300,000 $h^{-1}$ to about 600,000 $h^{-1}$. In embodiments, the space velocity can be about 60,000 $h^{-1}$, about 66,000 $h^{-1}$, about 72,000 $h^{-1}$, about 75,000 $h^{-1}$, about 78,000 $h^{-1}$, about 84,000 $h^{-1}$, about 90,000 $h^{-1}$, about 105,000 $h^{-1}$, about 120,000 $h^{-1}$, about 300,000 $h^{-1}$, about 330,000 $h^{-1}$, about 360,000 $h^{-1}$, about 375,000 $h^{-1}$, about 390,000 $h^{-1}$, about 420,000 $h^{-1}$, about 450,000 $h^{-1}$, about 525,000 $h^{-1}$, or about 600,000 $h^{-1}$. For example, space velocity can be measured as LHSV=volume flow rate of feed in sccm/catalyst loading in cc. For a 0.5 wt % Pt catalyst loading and a flow rate of 200 sccm of feed, the catalyst used for testing was ~0.15 g and the estimated catalyst loading in cc is 0.04 $cm^3$. So the LHSV is (200 sccm*60)/0.04 $cm^3$=300,000 $h^{-1}$. For example, a 0.1 wt % Pt catalyst and a flow rate of 250 sccm of feed, five times more catalyst was tested, so the estimated catalyst loading in cc is 0.2 $cm^3$. So the LHSV is (250 sccm*60)/0.2 $cm^3$=75,000 $h^{-1}$.

In embodiments, the equilibrium conversion of alkane to alkene can be about 15% to about 50%, or about 20% to about 45%, or about 25% to about 40%, or about 30% to about 40%. In embodiments, the equilibrium conversion of alkane to alkene can be about 30% to about 40%.

In embodiments, the catalyst experiences a total amount of thermal cracking of less than about 3% after about 20 hours. In embodiments, the catalyst experiences a total amount of thermal cracking of less than about 1% after about 20 hours.

The alkane dehydrogenation catalysts of the disclosure can have a selectivity to alkenes of greater than about 70%. In embodiments, the alkane dehydrogenation catalyst can have a selectivity to alkenes of greater than about 85%. For example the alkane dehydrogenation catalyst can have a selectivity to alkenes of about 70% to 100%, or about 70% to about 99.9%, or about 70% to about 99%, or about 70% to about 95%, or about 85% to 100%, or about 85% to about 99%, or about 85% to about 95%, or about 85% to about 90%, such as, 70%, 75%, 80%, 85%, 90%, 95%, 98%, 99%, 99.9%, 100%.

Examples of atomic layer deposition methodologies and conditions which can be applicable for the use of the methods of the disclosure, can be found in the following publications, which are incorporated herein by reference, U.S. Pat. Nos. 9,284,643 & 9,546,424.

Chemisorption Test Method $H_2$ chemisorption was performed using a Micromeritics ASAP 2020 analyzer using the double isotherm method (Perrichon et al., *Appl Catal a-Gen* 2004, 260 (1), 1-8). The first isotherm provides the total amount of chemisorbed hydrogen; the second isotherm gives the reversible chemisorbed hydrogen. The difference between the two isotherms is the irreversibly chemisorbed hydrogen on the platinum surface.

For example, the $H_2$ chemisorption can be tested by using a sample (i.e., alkane dehydrogenation catalyst) that was reduced in $H_2$ at 773 K and re-oxidized at 313 K. The $H_2$ chemisorption was performed at 313 K to generate the first isotherm, which gives the total amount of chemisorbed hydrogen. At the same temperature, the second isotherm was generated, which gives the reversible bound chemisorbed hydrogen, the difference between the two isotherms giving the irreversible chemisorbed hydrogen, which corresponds to hydrogen adsorbed on the catalyst surface (e.g., Pt). The two isothermal curves were drawn in the 70 to 400 mmHg pressure domain.

EXAMPLES

In the examples below, characterization of the resulting catalysts and methods of converting alkanes to alkenes were characterized using the following techniques.

Steam Treatment—To simulate long term deactivation, all newly made alkane dehydrogenation catalysts were subjected to steaming at 700° C. The procedure used was as follows: A fraction of the alkane dehydrogenation catalyst was placed in a ceramic boat. The ceramic boat was placed inside of a horizontal quartz tube located inside of a horizontal tube furnace. Dry nitrogen was flowed through the reactor while the furnace was heated to the steaming temperature. When the desired temperature was reached, the flow of nitrogen was diverted so that it flowed through a water bubbler to saturate the gas with water. The $N_2$/water gas was then flowed over the catalyst for the prescribed time.

Example 1

Catalyst synthesis. Alumina extrudates were synthesized by peptizing Versal-251, a boehmite alumina produced by UOP with nitric acid and extrusion as 1/16" cylinders. The dried extrudates were calcined at temperatures ranging from 500° C. to 1185° C. to generate $Al_2O_3$ bases with varying surface area and porosity. Pt was impregnated at 0.1 wt % and 0.5 wt % via standard incipient wetness procedures featuring solutions of Pt precursor. Prior to Pt impregnation, the $Al_2O_3$ extrudates had been calcined at 500° C. (ultra-high SA), 600° C. (high SA), 750° C. (medium SA), 1050° C. (low SA), or 1185° C. (ultra-low SA) to adjust the surface area. After impregnation, the catalysts, comprising Pt, were oxidized at a temperature of about 500° C. in air, and prior to next steps, then reduced in an atmosphere comprising $H_2$ at a temperature of about 500° C. For catalysts comprising extrudates previously calcined at 1185° C., this oxidation and reduction was performed at 250° C. $Al_2O_3$ ALD was performed on the Pt/$Al_2O_3$ catalyst extrudates in a fixed bed ALD reactor at 200° C. using alternating exposure to trimethylaluminum (TMA) and deionized water on a Prometheus P6 reactor (available from Forge Nano). $TiO_2$ ALD was performed on the same reactor using alternating exposure to titanium tetrachloride ($TiCl_4$) and deionized water at 150° C. An integrated mass spectrometer on the reactor exhaust monitored the ALD reaction in real time. Prior to deposition, the extrudates were degassed under nitrogen flow at 300° C. to remove adventitious water from the surfaces before lowering the temperature to the deposition temperature and proceeding with the ALD process. The catalysts below are categorized using shorthand shown here: ncAlO/xPt/m, wherein the n represents the number of $Al_2O_3$ ALD cycles (c), x represents the initial Pt loading (in wt. %), and m represents the catalyst support $Al_2O_3$ extrudates name: ultra-high SA=280 $m^2$/g; high SA=256 $m^2$/g; medium SA=211 $m^2$/g; low SA=90 $m^2$/g; ultra-low SA=8 $m^2$/g.

Characterization. $N_2$ physisorption were measured at 77 K with a Micromeritics ASAP 2020 analyzer to characterize the specific surface area and the pore size changes. Prior to the measurement, the samples were degassed overnight at 250° C. Thermogravimetric analysis (TA Instruments, Discovery TGA 5500) was used to investigate the moisture loss from the extrudates. In the TGA experiments, around 5 mg of an extrudate were placed in a crucible. The crucible was heated from room temperature to 700° C. at the rate of 10° C./min in ultra-high purity argon (99.999%) at a flow rate of 10 mL/min. Elemental compositions of the samples were determined by inductively coupled plasma (ICP) mass spectroscopy. Scanning transmission electron microscopy (STEM) images were taken at Electron Microscopy Center at Argonne National Laboratory using an FEI Talos Scanning Transmission Electron Microscope. The Pt particle sizes were determined using ImageJ software by counting about 100 to 200 particles from the images for each sample. The STEM is equipped with an energy-dispersive spectrometer (EDS). The lamellas for EDS mapping were prepared by using the Zeiss 1540XB focused ion beam-scanning electron microscopy (FIB-SEM). $H_2$ chemisorption was performed using a Micromeritics ASAP 2020 analyzer using the double isotherm method (Perrichon et al., Appl Catal a-Gen 2004, 260 (1), 1-8). The first isotherm provides the total amount of chemisorbed hydrogen; the second isotherm gives the reversible chemisorbed hydrogen. The difference between the two isotherms is the irreversibly chemisorbed hydrogen on the platinum surface. Diffuse Reflectance Infrared Fourier Transform Spectroscopy (DRIFTS) was acquired using a Thermo Scientific Nicolet iS50 FTIR spectrometer equipped with an iS50 Automated Beam splitter exchanger (ABX). Catalysts were first reduced at 500° C. for 1 h in 2.8% $H_2$/Ar, then exposed to 30 mL/min 1% CO/He for 10 min and purged with 30 mL/min He. The spectra were collected after the He flush every 2 min. After that, sample was exposed to 30 mL/min air for 1 h, purged with He for 20 min and then reduced in 2.8% $H_2$/Ar for 1 h. After reduction, the sample was exposed to 30 mL/min 1% CO/He for 10 min and purged with 30 mL/min He. The spectra were collected right after the He flush for every 2 min. X-ray Absorption Spectroscopy (XAS) measurements were conducted at the Pt L3 edge (~11 564 eV) at beamline 10-BM of the Materials Research Collaborative Access Team (MR-CAT) at the Advanced Photon Source (APS) at Argonne National Laboratory. The XAS spectra were recorded in the transmission mode. The samples were pressed into a cylindrical holder that can hold six samples simultaneously. The loading of the sample was optimized to achieve a step height of 1. Before the measurement, the samples were fully reduced in 3.5% $H_2$ in helium at 523 K for 30 min, and subsequently cooled to room temperature in ultra-high purity helium.

Example 2

Measurement of catalytic activity. The catalytic reaction for propane dehydrogenation at atmospheric pressure was carried out in a vertical quartz tubular reactor with a diameter of 10 mm. The quartz tube reactor was placed within a furnace. The catalyst was supported on quartz wool with an internal thermocouple monitoring the temperature of the catalyst bed. Approximately 120 mg of 0.5% Pt catalysts and 600 mg of 0.1% Pt catalysts were crushed to 60-80 mesh and then loaded for testing. For catalysts with ALD overcoating, the amount of catalysts added was adjusted to keep the same Pt content in the reactor based on the Pt loading from ICP analysis. Two grams of quartz sand (80 mesh size) was used to dilute the catalyst to improve the temperature uniformity. Before the measurement, the catalyst was reduced in 10% $H_2$ for 0.5 h at 500° C. The ALD overcoated catalyst, as prepared in Example 1, was calcined in air for 1 h before the reduction. The reactant mixture consisted of 50/50 vol % of hydrogen (Airgas, 99.999%) and propane (Airgas, 99.5%), with a total flow of 260 mL/min. The reaction was carried out at 600° C. The temperature was monitored by a thermocouple inserted into the catalyst bed. The concentration of the reactants and products was measured by an online gas chromatograph (GC, Agilent 6890) equipped with a flame ionization detector (FID) and a thermal conductivity detector (TCD). The propane conversion, propylene selectivity, and propylene yield were calculated directly as follows:

$$C_3H_8 \text{ Conversion} = \frac{\text{moles of } C_3H_8 \text{ }_{in} - \text{moles of } C_3H_8 \text{ }_{out}}{\text{moles of } C_3H_8 \text{ }_{in}} \times 100\%$$

$$C_3H_6 \text{ Selectivity} = \frac{\text{moles of } C_3H_6}{\text{moles of } C_3H_6 + \dfrac{\text{moles of } C_2}{3/2} + \dfrac{\text{moles of } CH_4}{3}} \times 100\%$$

$$C_3H_6 \text{ Yield} = C_3H_8 \text{ Conversion} \times C_3H_6 \text{ selectivity} \times 100\%$$

Figure 5A:
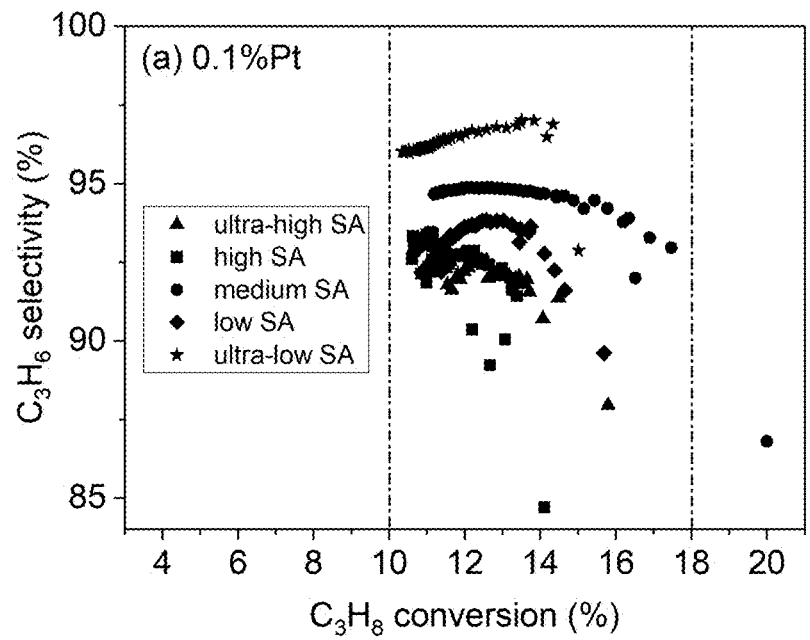
FIGS. 5A and 5B are graphs showing the C$_3$H$_8$ conversion versus C$_3$H$_6$ selectivity for non-ALD overcoated (A) 0.1% Pt and (B) 0.5% Pt catalysts. (Data was collected for 20 h with interval of 20 mins; to normalize the Pt loading for testing, the amount of 0.1% Pt catalysts loaded is 5 times more than the 0.5% Pt catalysts)
Figure 5B:
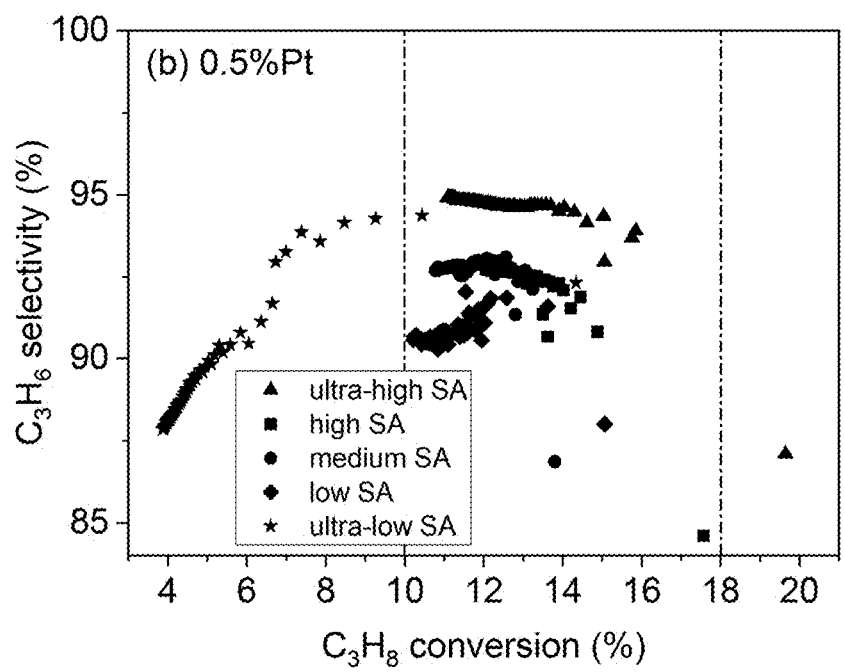
Figure 6A:
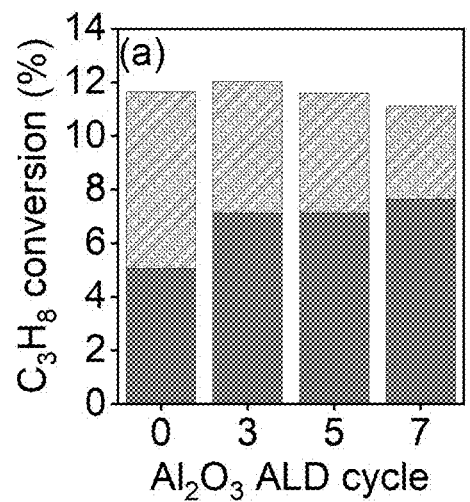
FIGS. 6A-6D are graphs showing C$_3$H$_8$ conversion versus Al$_2$O$_3$ ALD cycles at the 10$^{th}$ hour for 0.1% Pt catalysts on supports with (A) ultra-high SA, (B) high SA, (C) medium SA, and (D) low SA (gray bar: C$_3$H$_8$ conversion and C$_3$H$_6$ yield for steamed catalysts; hashed bar: change in C$_3$H$_8$ conversion and C$_3$H$_6$ yield between fresh and steamed catalysts; 0 cycle represents the catalysts without ALD overcoating)
Figure 6B:
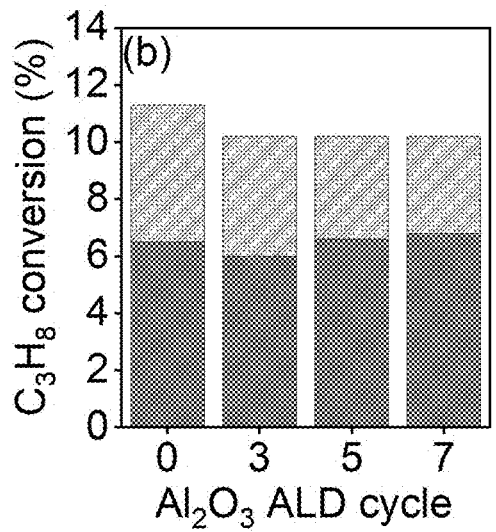
Figure 6C:
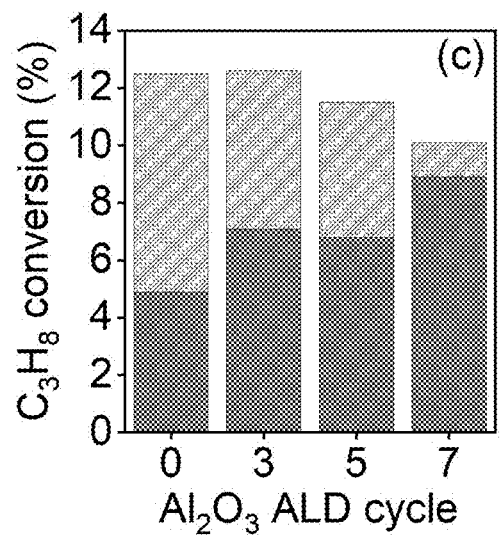
Figure 6D:
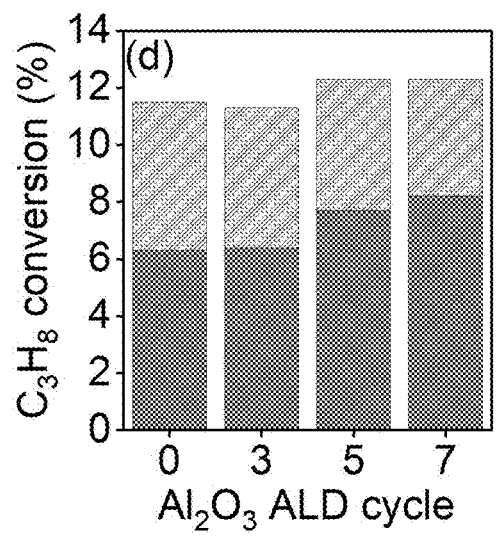
Figure 6E:
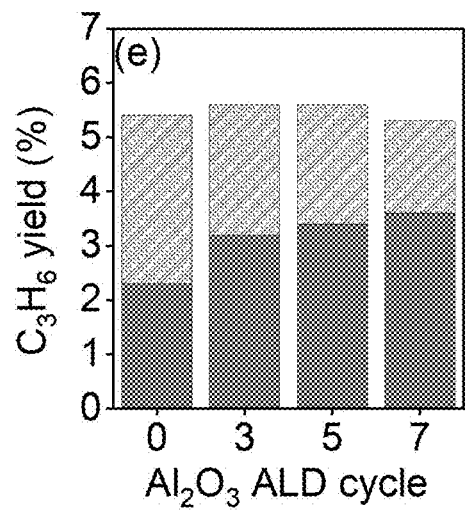
FIGS. 6E-6H are graphs showing C$_3$H$_6$ yield versus Al$_2$O$_3$ ALD cycles at 10$^{th}$ hour for 0.1% Pt catalysts on supports with (E) ultra-high SA, (F) high SA, (G) medium SA, and (H) low SA.
Figure 6F:
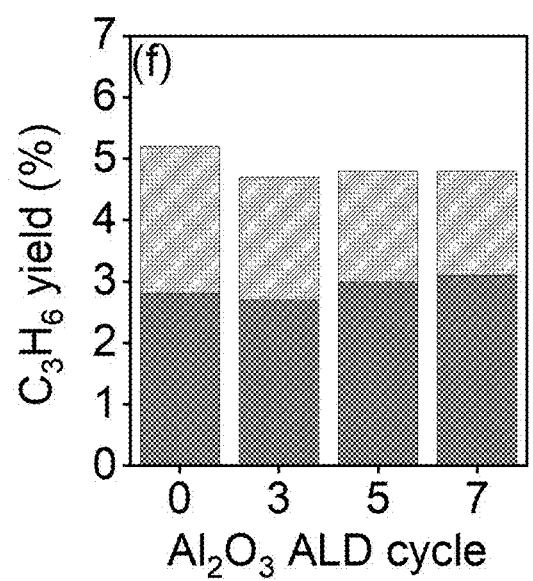
Figure 6G:
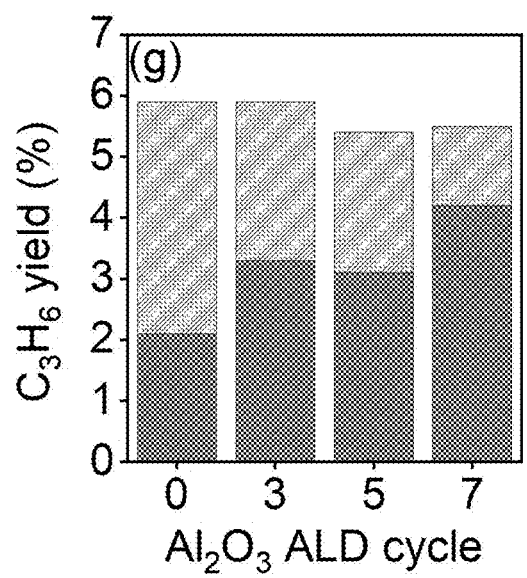
Figure 6H:
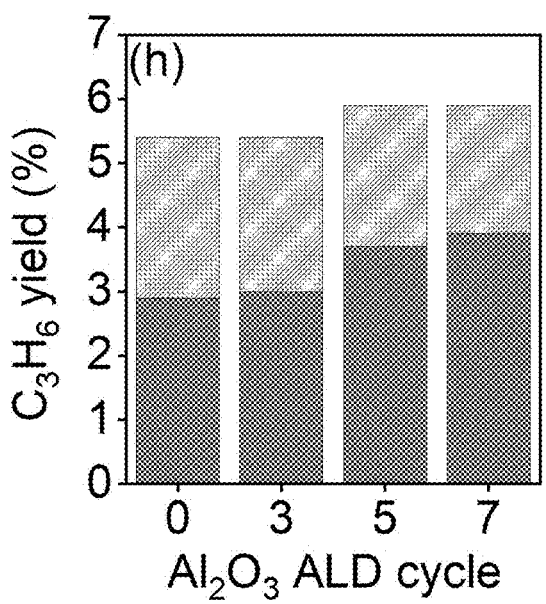
Figure 6I:
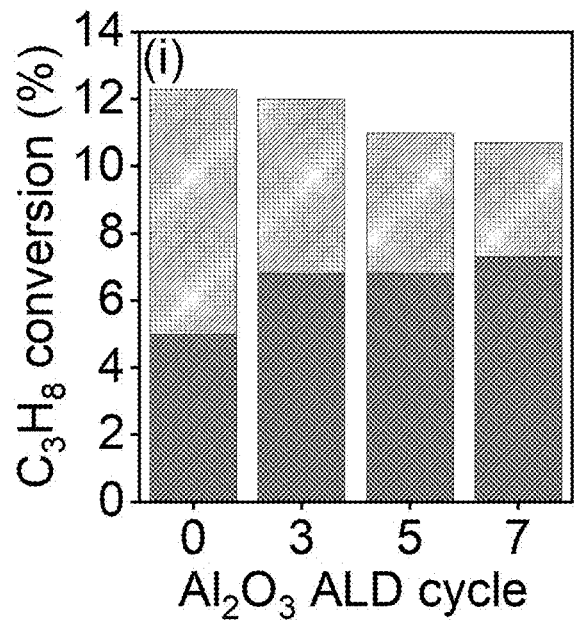
FIGS. 6I-6L are graphs showing C$_3$H$_8$ conversion versus Al$_2$O$_3$ ALD cycles at the 10$^{th}$ hour for 0.5% Pt catalysts on supports with (I) ultra-high SA, (J) high SA, (K) medium SA, and (L) low SA (gray bar: C$_3$H$_8$ conversion and C$_3$H$_6$ yield for steamed catalysts; hashed bar: change in C$_3$H$_8$ conversion and C$_3$H$_6$ yield between fresh and steamed catalysts; 0 cycle represents the catalysts without ALD overcoating)
Figure 6J:
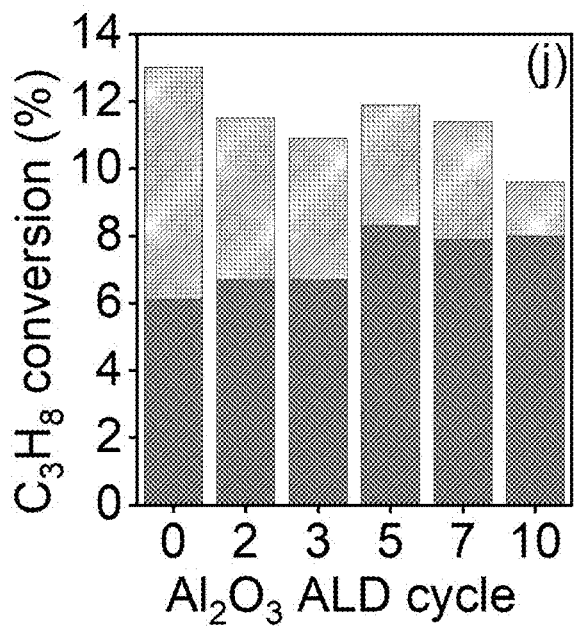
Figure 6K:
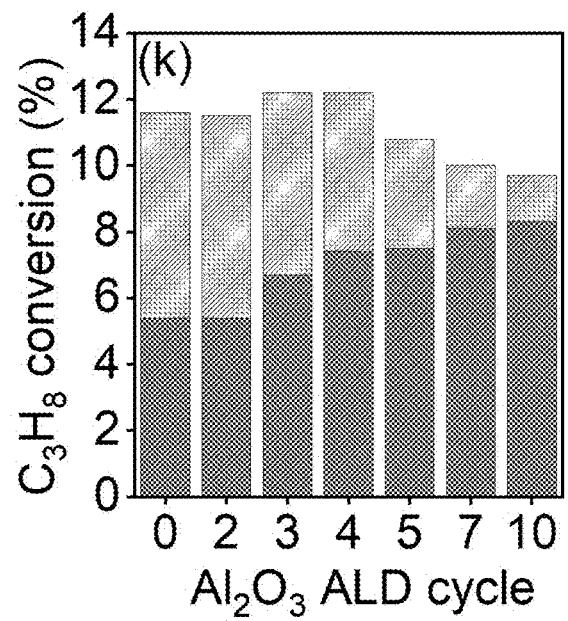
Figure 6L:
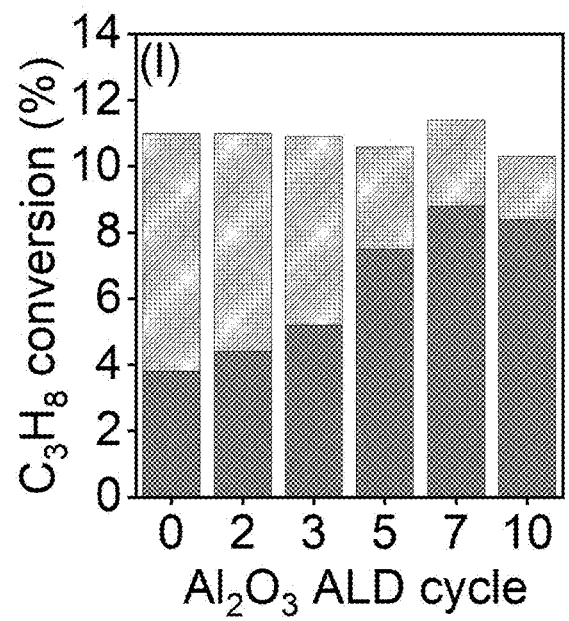
Figure 6M:
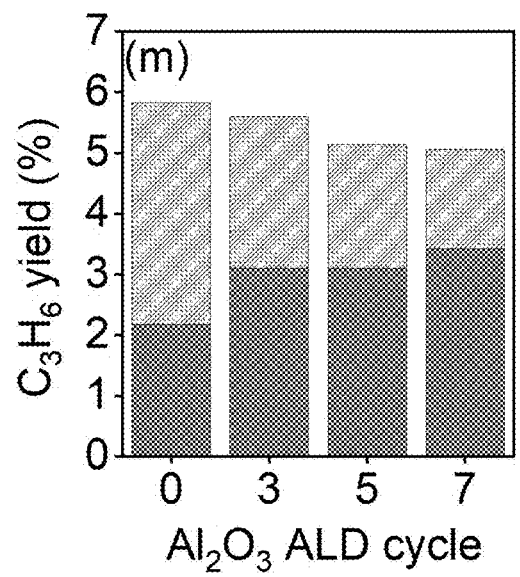
FIGS. 6M-6P are graphs showing C$_3$H$_6$ yield versus Al$_2$O$_3$ ALD cycles at the 10$^{th}$ hour for 0.5% Pt catalysts on supports with (M) ultra-high SA, (N) high SA, (O) medium SA, and (P) low SA (gray bar: C$_3$H$_8$ conversion and C$_3$H$_6$ yield for steamed catalysts; hashed bar: change in C$_3$H$_8$ conversion and C$_3$H$_6$ yield between fresh and steamed catalysts; 0 cycle represents the catalysts without ALD overcoating)
Figure 6N:
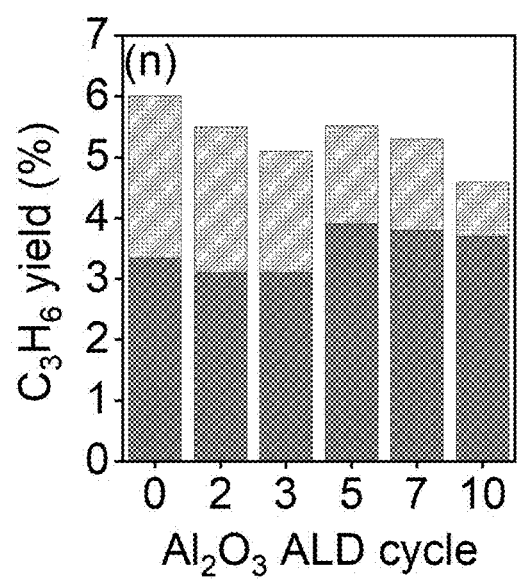
Figure 6O:
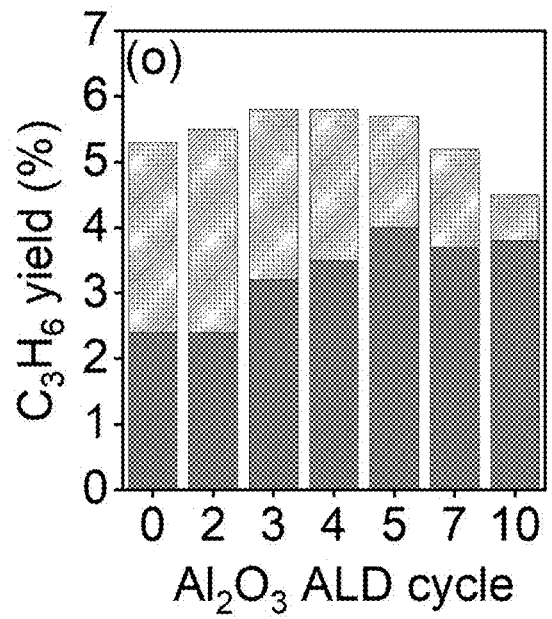
Figure 6P:
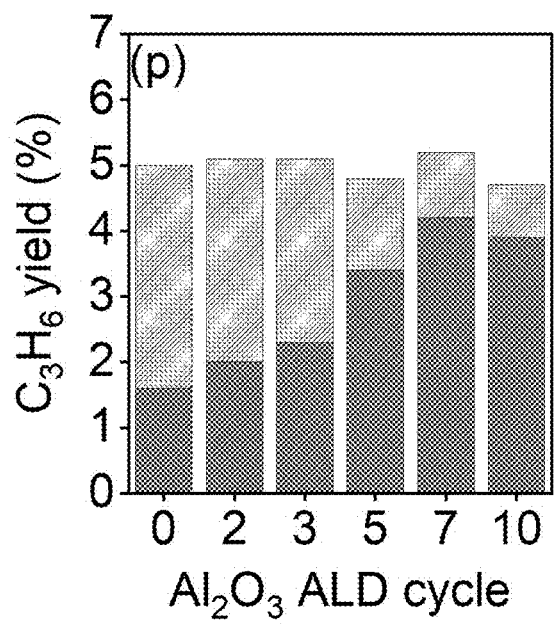

Catalyst Performance. FIG. 5 shows the $C_3H_8$ conversion vs $C_3H_6$ selectivity for 0.1% and 0.5% Pt catalysts prior to ALD modification, which were prepared according to Example 1. The $C_3H_8$ conversion decreased from 18% to 10% for all catalysts except for catalyst 0.5 Pt/ultra-low SA (which decreased from 10% to 4%). The low $C_3H_8$ conversion (<10%) was due to the formation of unevenly distributed larger Pt nanoparticles (cf. Table 2), since at the same Pt loading, increases in the Pt particle size led to a decrease in the number of surface Pt sites. Pt nanoparticle sintering was another possible reason of low conversion for this ultra-low surface area catalyst, which had a higher probability of encountering other Pt during the reaction. Thus, ALD overcoating was not applied for catalysts on ultra-low surface area support because the $C_3H_8$ conversion dropped to 4%. The $C_3H_6$ selectivity for all catalysts is above 85%.

The average Pt nanoparticles size remained at 0.88±0.11 nm after 20 h under reaction conditions for a non-ALD overcoated catalyst (0.5 Pt/medium SA). Comparatively, the fresh versus steamed catalysts (0.92±0.19 nm, derived from STEM images), had no obvious visible change of the Pt nanoparticles. Since even 20 hr on stream in the lab reactor cannot simulate long term catalyst deactivation, steam treatment was used to simulate the long-term effects (weeks/months) under commercial reaction conditions. The average Pt nanoparticles size after 1 h steam treatment at 700° C. was 1.96±1.18 nm, which showed the growth of Pt nanoparticles after steaming. In addition, the decrease in chemisorbed $H_2$ amount in FIG. 4 (c-f) also suggested agglomeration of the Pt nanoparticles. Thus, in testing the $C_3H_8$ conversion change and longevity improvement after ALD overcoating, two equal amounts of each catalyst were tested without and with steam pretreatment. Since the Pt loading would be changed after ALD overcoating, to load the same amount of Pt for testing, the amount of each catalyst was adjusted based on the Pt loading from ICP measurement. The $C_3H_8$ conversion and $C_3H_6$ yield at the $10^{th}$ hour during the reaction are shown in FIG. 6. The gray bar height represents the $C_3H_8$ conversion and $C_3H_6$ yield for each steamed catalyst, while the hashed bar height represents the drop (absolute value) of $C_3H_8$ conversion and $C_3H_6$ yield after steaming compared to fresh catalysts, thus, the total bar height (combine gray and hashed bar height) represents the $C_3H_8$ conversion and $C_3H_6$ yield for each fresh catalyst (without steam pretreatment). Generalizing, for all fresh catalysts, it was notable that the $C_3H_8$ conversion and $C_3H_6$ yield were not substantially changing as a function of ALD coating thickness, which suggested the overcoated $Al_2O_3$ by ALD does not block the active Pt sites. For some of the ALD overcoated catalysts, the $C_3H_8$ conversion and $C_3H_6$ yield were slightly higher than non-overcoated ones, which was probably because of the uneven distributed Pt nanoparticles. Contrarily, the $C_3H_8$ conversion and $C_3H_6$ yield of the steamed catalysts (gray bar height) increased as a function of ALD thickness. Thus, the change in $C_3H_8$ conversion and $C_3H_6$ yield between the fresh and steamed catalysts (hashed bar height) was decreasing as a function of increasing ALD thickness which suggested that the improvement in catalysts longevity after ALD overcoating.

Figure 7:
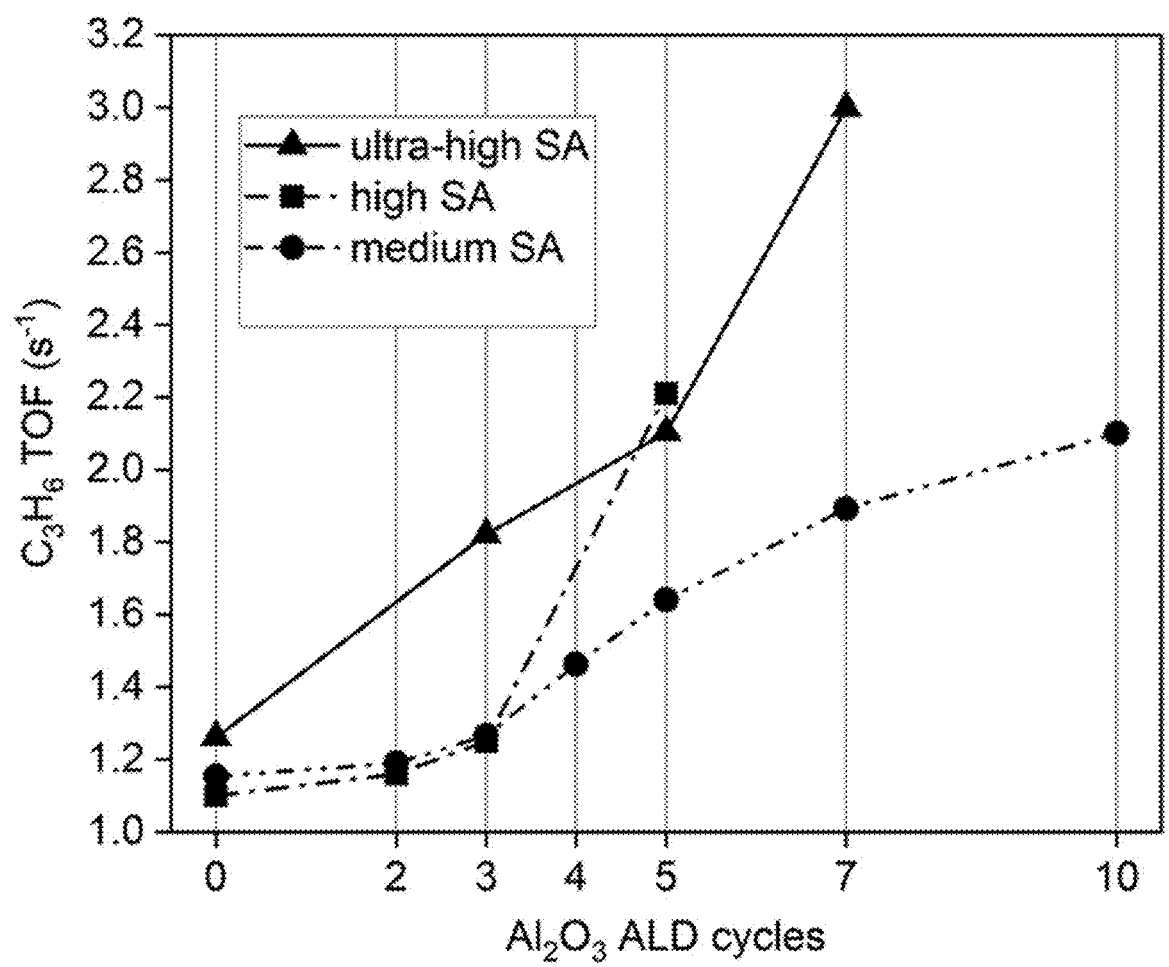
FIG. 7 is a graph of the turnover frequency (TOF) of C$_3$H$_6$ at the 10$^{th}$ hour during the reaction for 0.5% Pt loaded catalysts versus Al$_2$O$_3$ ALD cycle, comparing catalyst supports having ultra-high, high, and medium surface areas.
Figure 8A:
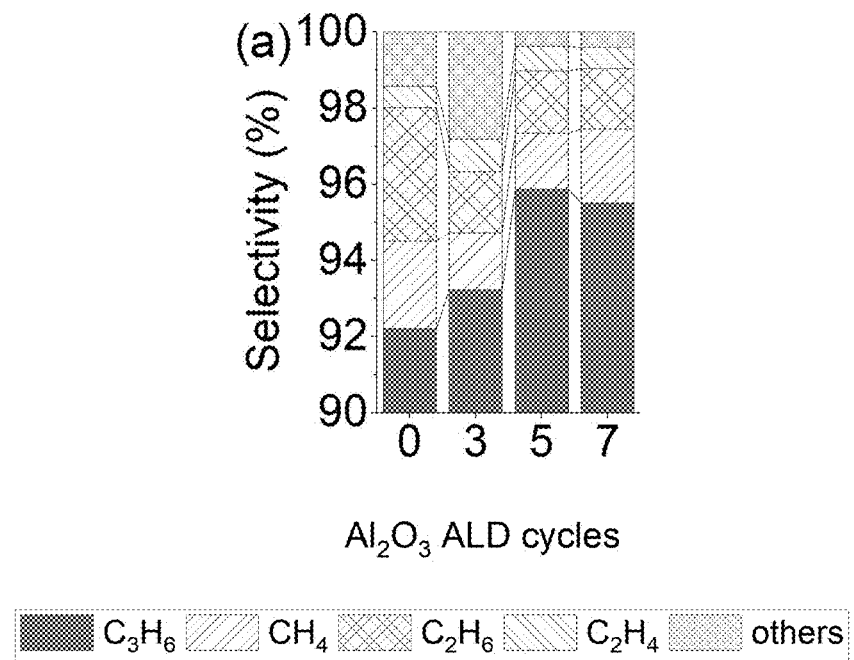
FIGS. 8A-8D are graphs of the products selectivity for fresh 0.1% Pt catalysts on supports with (A) ultra-high SA, (B) high SA, (C) medium SA, and (D) low SA.
Figure 8B:
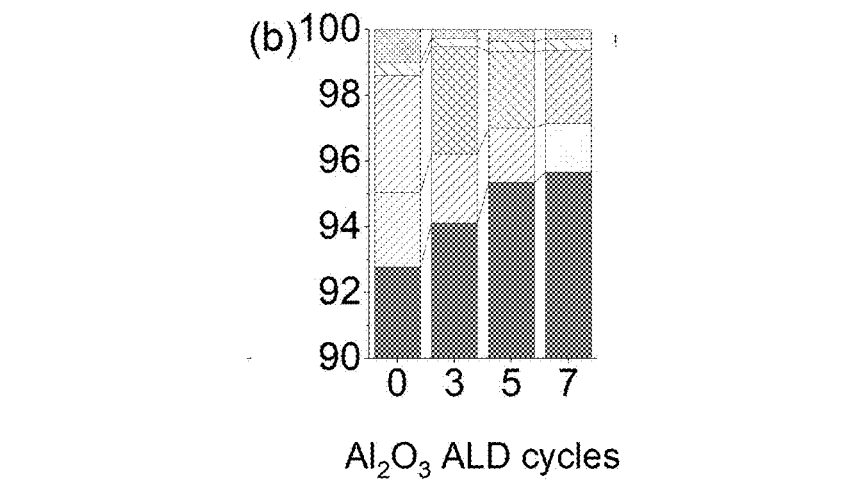
Figure 8C:
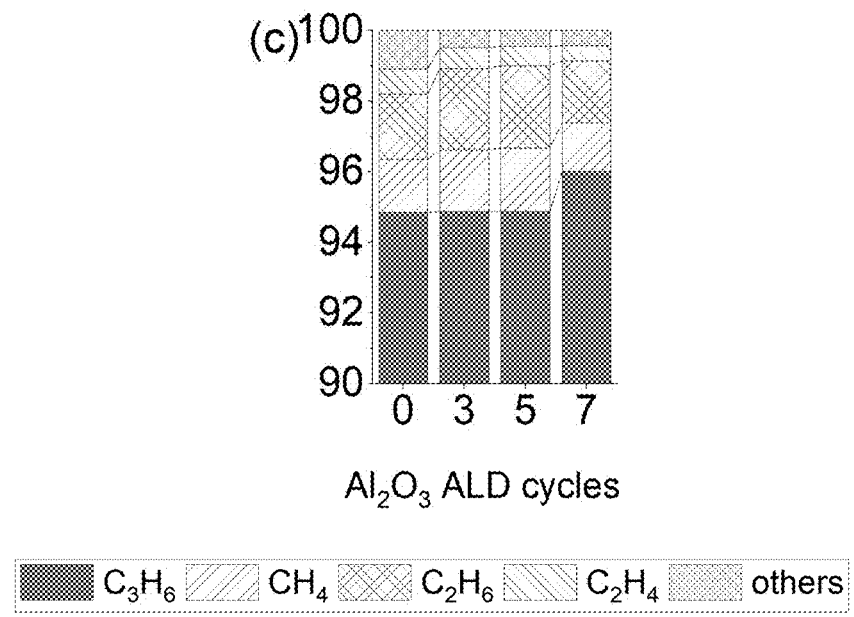
Figure 8D:
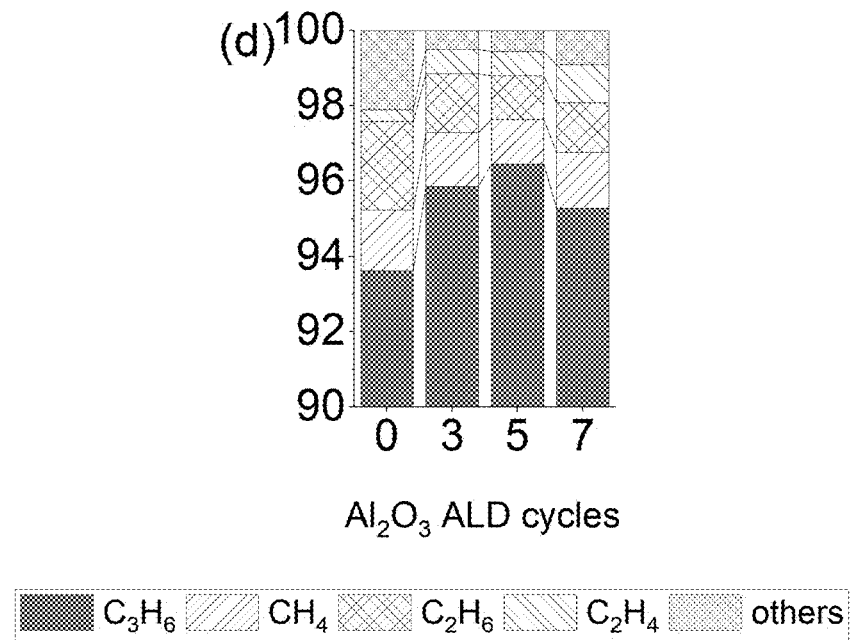
Figure 8E:
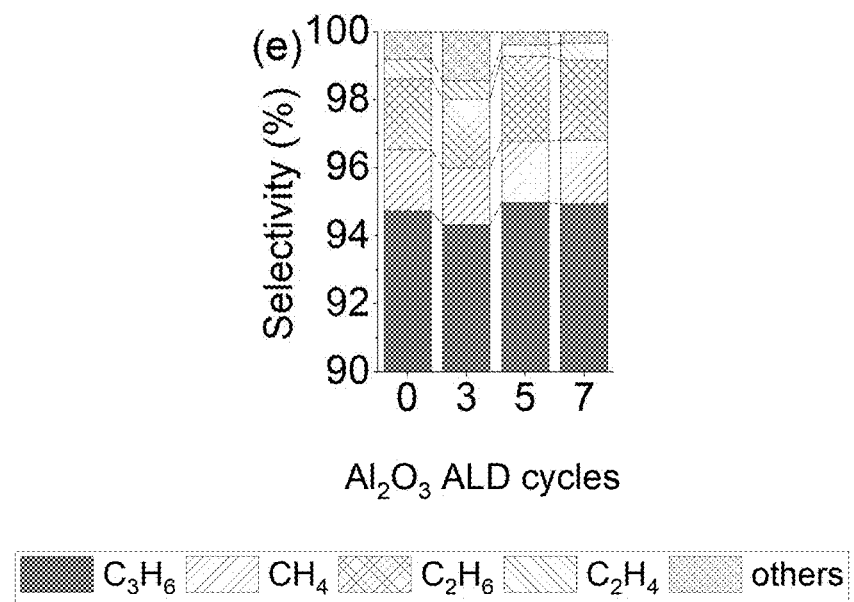
FIGS. 8E-8H are graphs of the products selectivity for fresh 0.5% Pt catalysts on supports with (E) ultra-high SA, (F) high SA, (G) medium SA, and (H) low SA.
Figure 8F:
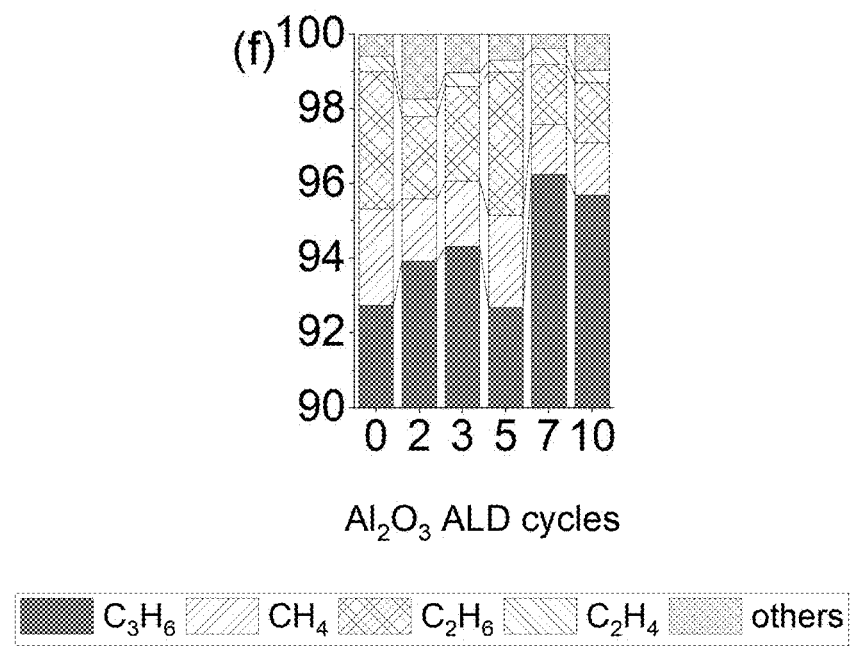
Figure 8G:
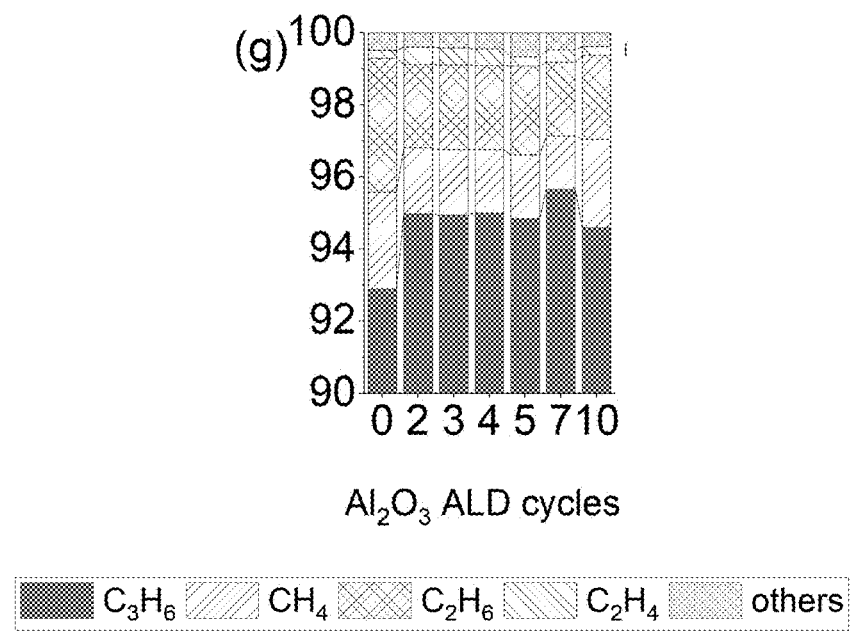
Figure 8H:
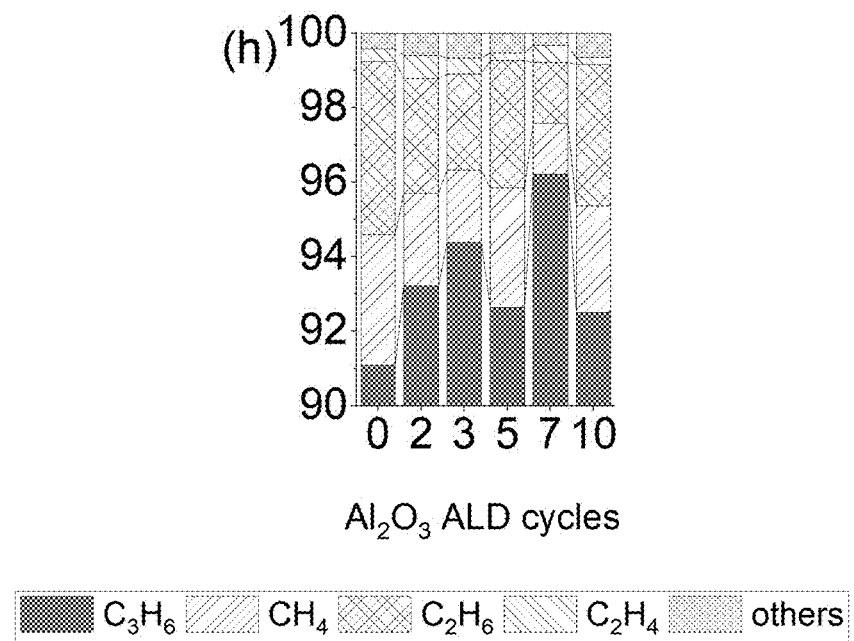

Using the results from the $H_2$ chemisorption, the turnover frequency (TOF, $s^{-1}$) of $C_3H_6$ after 10 hours on stream was normalized based on the amount of surface exposed Pt atoms after air annealing in FIG. 4. FIG. 7 showed that the $C_3H_6$ TOF increased with the increase of $Al_2O_3$ ALD cycles. If we assume all the surface Pt atoms were active sites for $C_3H_6$ formation and the $Al_2O_3$ material deposited by ALD was inert, the TOF should remain the same. As shown in FIG. 6, the $C_3H_6$ yield was not substantially changed as a function of ALD cycles, thus, the increase in TOF after ALD coverage of surface Pt atoms suggested that the $Al_2O_3$ deposited by ALD blocked the less active Pt sites for $C_3H_6$ formation, while leaving the most active sites still exposed. The low-coordinated surface metal atoms (edge or corner) may be the sites for both metal sintering and coke formation. The overcoated $Al_2O_3$ appeared to selectively cover those low-coordinated sites, which explained the improvement in longevity as well as the $C_3H_6$ TOF. As shown in FIG. 8, the $C_3H_6$ selectivity maintained or slightly increased as a function of ALD cycles and accompanied by the decrease in selectivity for two major byproducts, $CH_4$ and $C_2H_6$. The product selectivities reported here corresponded to $C_3H_8$ conversion at ~12% for fresh catalysts and ~7% for steamed catalysts. The selectivities of $CH_4$ and $C_2H_6$ for each catalyst were very similar, suggesting that those two byproducts were mainly produced through a hydrogenolysis reaction since the molar ratio for those two byproducts is 1:1 ($C_3H_8$+ $H_2 \rightarrow C_2H_6+CH_4$). The slight increase in $C_3H_6$ selectivity was attributed to the inhibition of this hydrogenolysis reaction due to blockage of the low-coordinated surface Pt sites after $Al_2O_3$ ALD. For steamed catalysts, the products selectivity suggested the improvement in $C_3H_6$ selectivity after $Al_2O_3$ ALD decoration.

Example 3

Characterization of $Al_2O_3$ extrudates. In catalyst synthesis, using high surface area material as a support can help to disperse and stabilize Pt nanoparticles. However, in terms of ALD coating, low substrate surface area is favorable since it would take less time and amount of ALD precursors to saturate the substrate surface. To investigate the effects of the surface area of the support on the ALD overcoating process, $Al_2O_3$ extrudates were calcined at 500, 600, 750, 1050, or 1185° C. Table 1 shows that increasing the support calcination temperature results in a decrease in the surface area as well as the pore volume, falling from ~280 $m^2/g$ to ~8 $m^2/g$ as the consecutive phase transitions from $\gamma$-$Al_2O_3$ through $\Theta$-$Al_2O_3$ to $\alpha$-$Al_2O_3$ are observed by XRD (Wefers et al., *Alcoa Research Laboratories* 1987, *Alcoa technical paper, no.* 19, rev.). The moisture loss was seen to decrease as calcination temperature increased, which can be attributed to the loss of surface area and thus surface hydroxyls. Water loss was then used as a proxy for the amount of $Al(CH_2)_3$ required during the ALD overcoating step.

TABLE 1

Textural properties of $Al_2O_3$ extrudates derived
from $N_2$ physisorption and XRD results

| T[a] (° C.) | Total SA ($m^2/g$) | External SA ($m^2/g$) | Pore volume ($cm^3/g$) | Average Pore Size (nm) | XRD phase | Support name[b] |
|---|---|---|---|---|---|---|
| 500 | 280 | 274 | 0.70 | 6.8 | γ | ultra-high SA |
| 600 | 256 | 246 | 0.66 | 7.1 | γ | high SA |
| 750 | 211 | 198 | 0.64 | 8.3 | γ/θ | medium SA |
| 1050 | 90 | 83 | 0.51 | 16.1 | θ/α | low SA |
| 1185 | 8 | 7 | 0.03 | 15.6 | α | ultra-low SA |

[a] $Al_2O_3$ extrudates calcination temperature
[b] SA: surface area

Example 4

Characterization of Pt nanoparticles. FIG. 1 shows representative STEM images of the non-ALD overcoated Pt catalysts, as described in Example 1 prior to the ALD coating process, where the Pt nanoparticles were highly dispersed on support $Al_2O_3$ extrudates. The average Pt nanoparticles size are listed in Table 2. Except for catalyst 0c/0.5 Pt/ultra-low SA, which had the largest Pt nanoparticle size (1.12±0.36 nm) due to the limited surface area on which to disperse Pt. Other 0.1% and 0.5% Pt loaded catalysts had average nanoparticle sizes around 0.9 nm with narrow size distribution. The amount of the $H_2$ chemisorbed per Pt was similar for each 0.1% and 0.5% Pt catalyst, moreover, the increase in Pt loading (5 times more from 0.1% to 0.5%) led to around 5 times more $H_2$ chemisorbed (4.5 to 24.0 μmol/g), again demonstrating the formation of similar-sized Pt nanoparticles. The only exception was for catalyst 0c/0.5% Pt/ultra-low SA with larger and unevenly dispersed Pt nanoparticles formed, the amount of $H_2$ chemisorbed was only 15.9 μmol/g. Peak intensity of the Fourier transformed EXAFS spectra were known to reflect the average nanoparticles size (Lei et al., *Top Catal* 2011, 54 (5-7), 334-348). Peak intensities are similar among those four catalysts (0.1% and 0.5% Pt on both medium and ultra-high SA supports), again indicating the average Pt nanoparticles size was similar. For catalysts on ultra-low SA support, the higher peak intensity again suggested larger Pt nanoparticles formation.

TABLE 2

Summary of Pt nanoparticles size and
$H_2$ chemisorption results

| Sample | Average diameter (nm) | Amount of $H_2$ chemisorbed (μmol/g) |
|---|---|---|
| 0.1%Pt/ultra-high SA | 0.81 ± 0.13 | 4.5 |
| 0.1%Pt/high SA | 0.89 ± 0.13 | 4.5 |
| 0.1%Pt/medium SA | 0.90 ± 0.12 | 4.5 |
| 0.1%Pt/low SA | 0.87 ± 0.11 | 4.8 |
| 0.1%Pt/ultra-low SA | 0.92 ± 0.23 | 4.9 |
| 0.5%Pt/ultra-high SA | 0.88 ± 0.16 | 24.3 |
| 0.5%Pt/high SA | 0.92 ± 0.13 | 21.2 |
| 0.5%Pt/medium SA | 0.92 ± 0.19 | 24.0 |
| 0.5%Pt/low SA | 0.90 ± 0.13 | 28.4 |
| 0.5%Pt/ultra-low SA | 1.12 ± 0.36 | 15.9 |

Example 5

Figure 2:
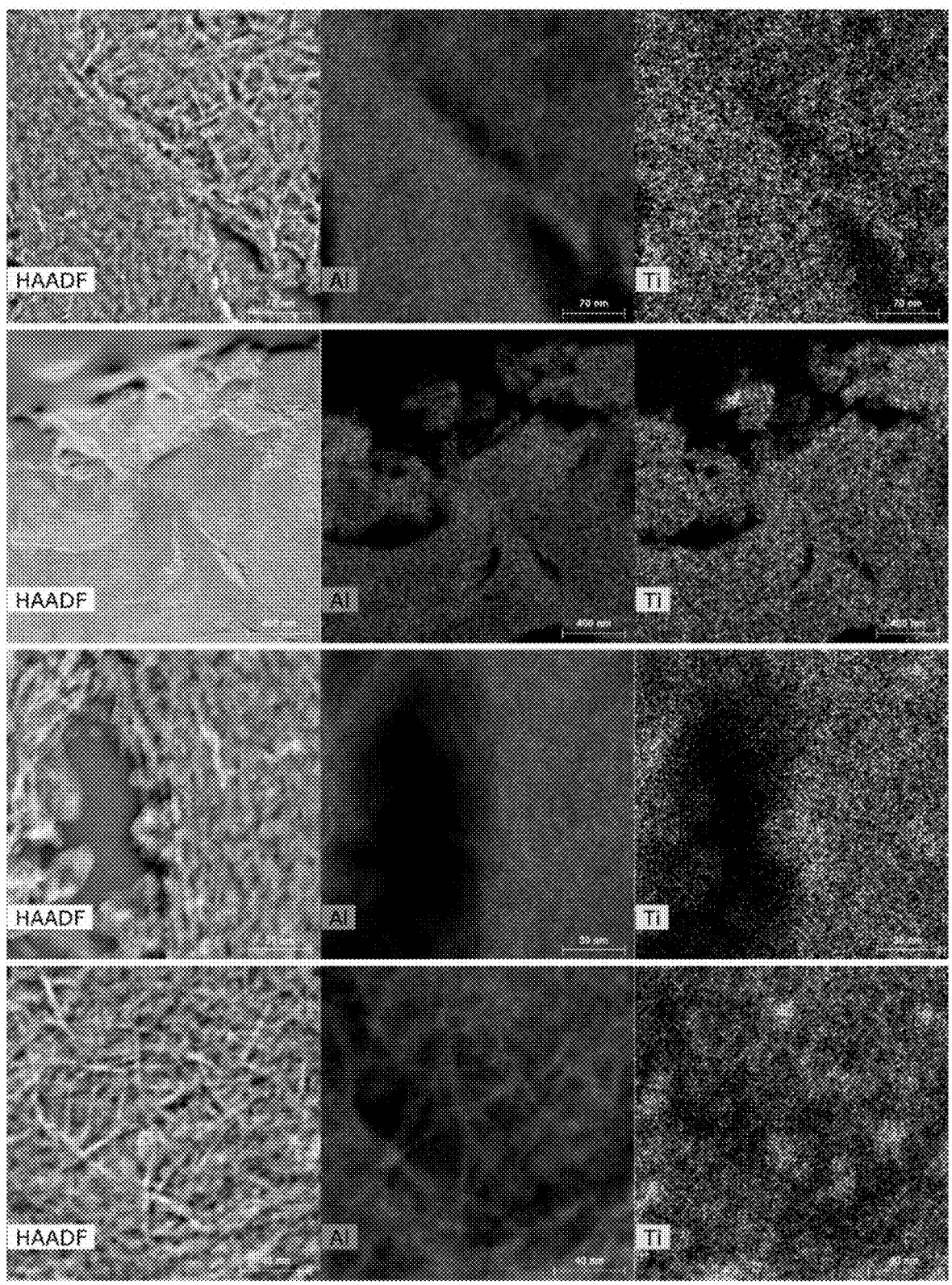
FIG. 2 includes dark field STEM images and corresponding EDS maps from four different parts of the alkane dehydrogenation catalyst (medium SA Al$_2$O$_3$ extrudates after 5 cycles of TiO$_2$ ALD) in accordance with embodiments of the disclosure.

Characterization of the material properties after ALD. Testing was done to understand precursor penetration into the $Al_2O_3$ extrudates. Since it was not feasible to distinguish $Al_2O_3$ deposited by ALD from $Al_2O_3$ extrudates, $TiO_2$ ALD ($TiCl_4$ and $H_2O$ as precursor at 150° C.) was utilized to understand precursor penetration behavior. To demonstrate the precise control of deposition at atomic level for both $Al_2O_3$ and $TiO_2$ ALD, ex situ spectroscopic ellipsometry was used to measure the thin film thickness after 50, 100, and 200 cycles of $Al_2O_3$ and $TiO_2$ ALD on clean Si (100) wafers. The thickness of $Al_2O_3$ and $TiO_2$ increased linearly as a function of ALD cycles with the growth rate of 1.2 and 0.4 Å per cycle, respectively. The growth rate for both ALD processes was the same as values reported in the literature (Ott et al., *Thin Solid Films* 1997, 292 (1-2), 135-144; Aarik et al., *Appl Surf Sci* 2001, 172 (1-2), 148-158). FIG. 2 displays the EDS mapping analysis of medium SA $Al_2O_3$ extrudates after 5 cycles of $TiO_2$ ALD. The samples were extracted from inside of the $Al_2O_3$ extrudates by removing the $Al_2O_3$ from the surface with the help of a micromanipulator using FIB-SEM. The EDS maps showed the homogeneous distribution of Ti across the $Al_2O_3$ extrudates porosity.

Figure 3A:
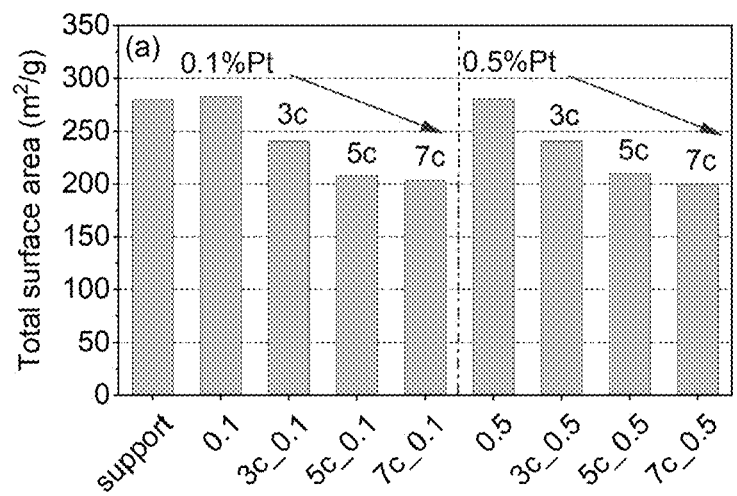
FIGS. 3A-3H are graphs showing the total surface area and the pore volume for alkane dehydrogenation catalyst in accordance with embodiments of the disclosure. The graphs show the total surface for 0.1% and 0.5% Pt catalyst loading on (A) ultra-high SA, (C) high SA, (E) medium SA, and (G) low SA supports. The graphs show the pore volume for 0.1% and 0.5% Pt catalyst loading on (B) ultra-high SA, (D) high SA, (F) medium SA, and (H) low SA supports.
Figure 3B:
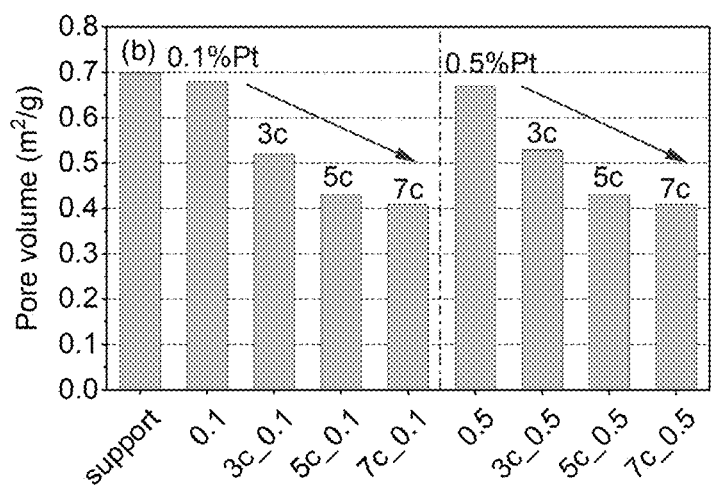
Figure 3C:
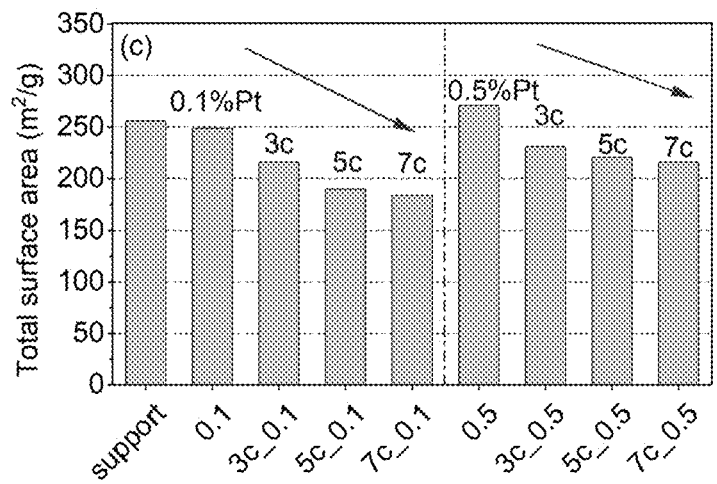
Figure 3D:
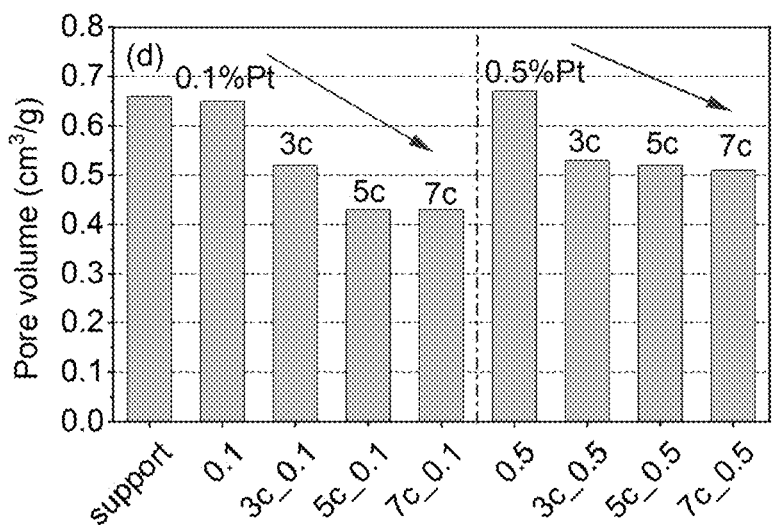
Figure 3E:
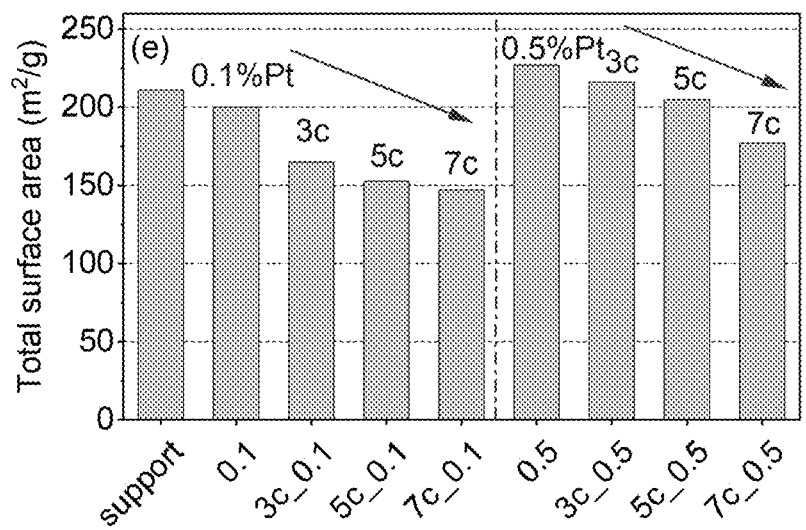
Figure 3F:
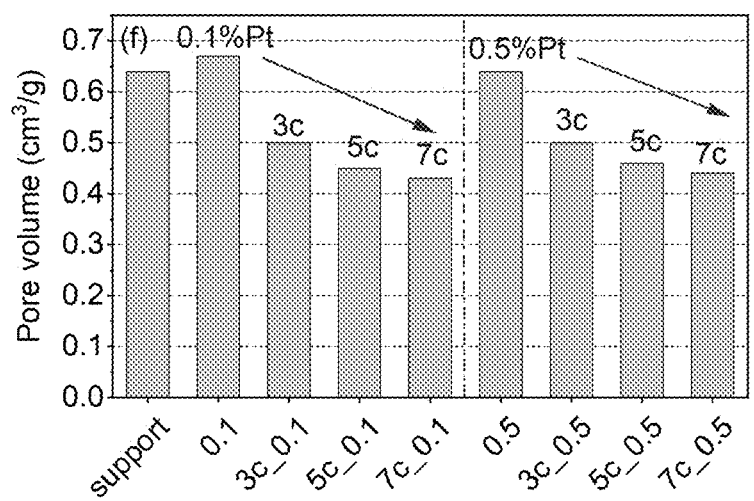
Figure 3G:
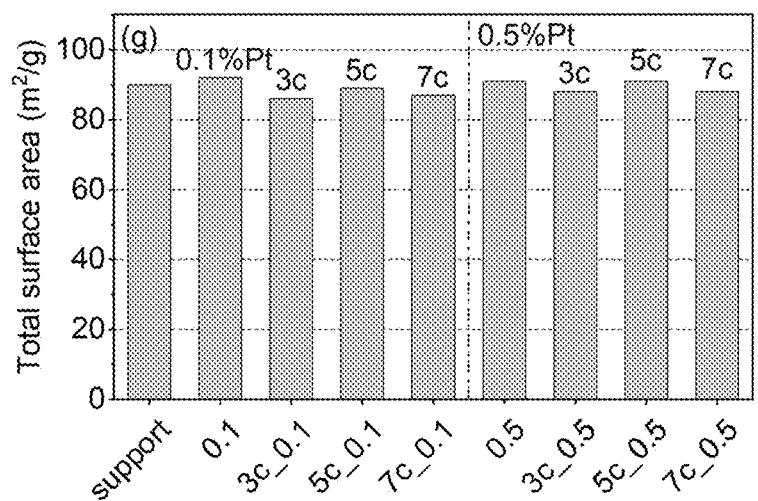
Figure 3H:
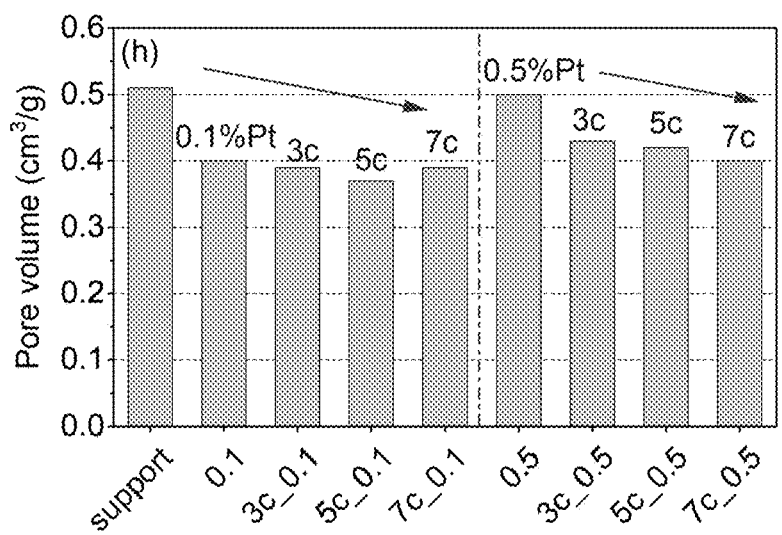
Figure 4A:
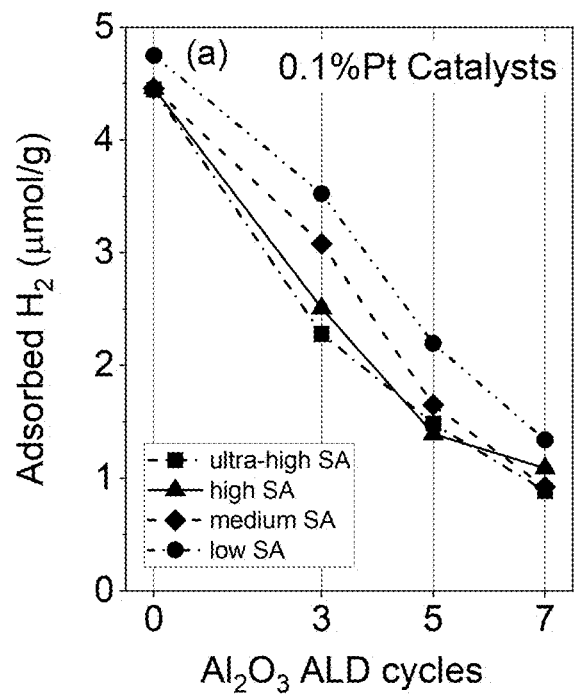
FIGS. 4A-4F are graphs showing the H$_2$ chemisorption results for the Al$_2$O$_3$ ALD overcoated catalysts in accordance with embodiments of the disclosure. The graphs are of the following catalysts: (A) 0.1% Pt and (B) 0.5% Pt, on ultra-high SA (squares), high SA (triangles), medium SA (diamonds), and low SA (circles) supports; (C) 0.5% Pt/ultra-high SA, (D) 0.5% Pt/high SA, (E) 0.5% Pt/medium SA, and (F) 0.5% Pt/low SA catalysts, samples after Al$_2$O$_3$ ALD overcoating (triangles); samples after air annealing (circles); samples after 1 h steam treatment (diamonds); samples after 4 h steam treatment (squares)
Figure 4B:
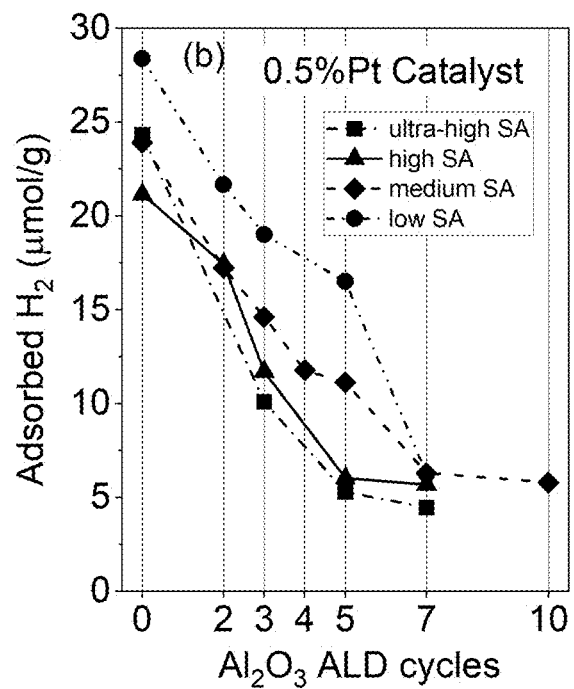
Figure 4C:
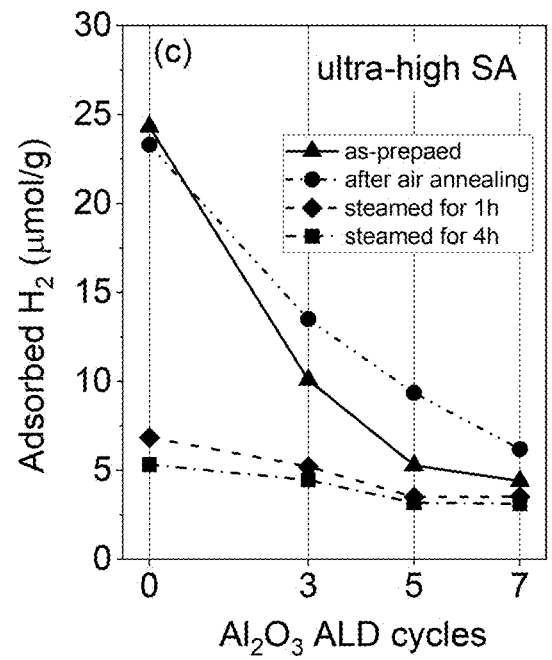
Figure 4D:
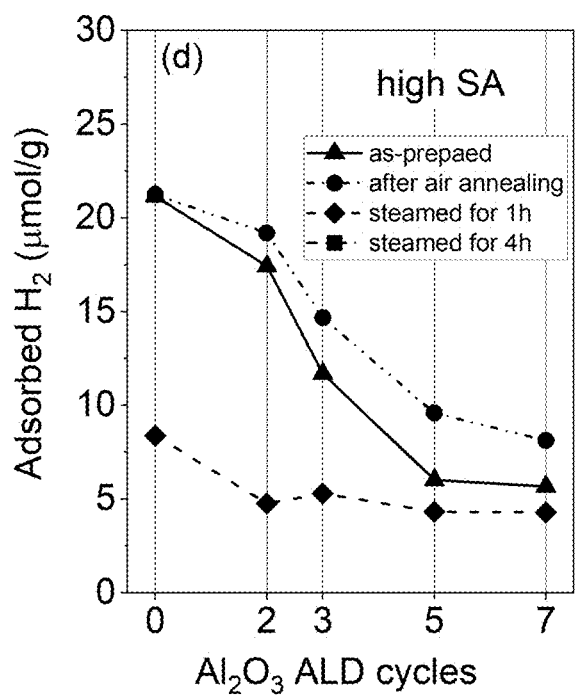
Figure 4E:
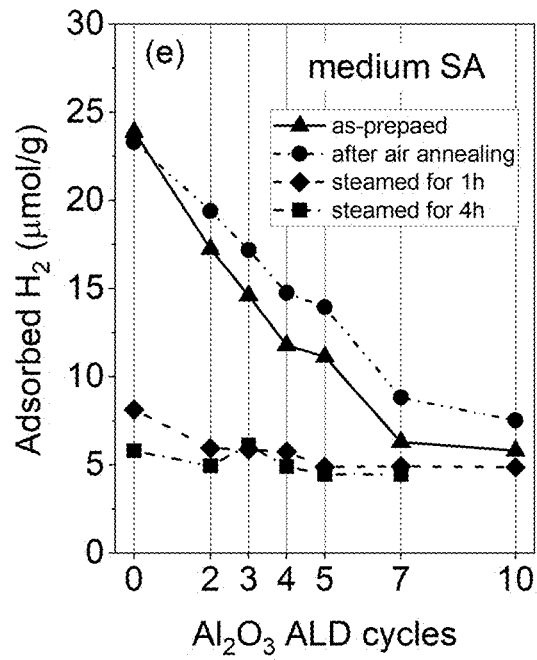
Figure 4F:
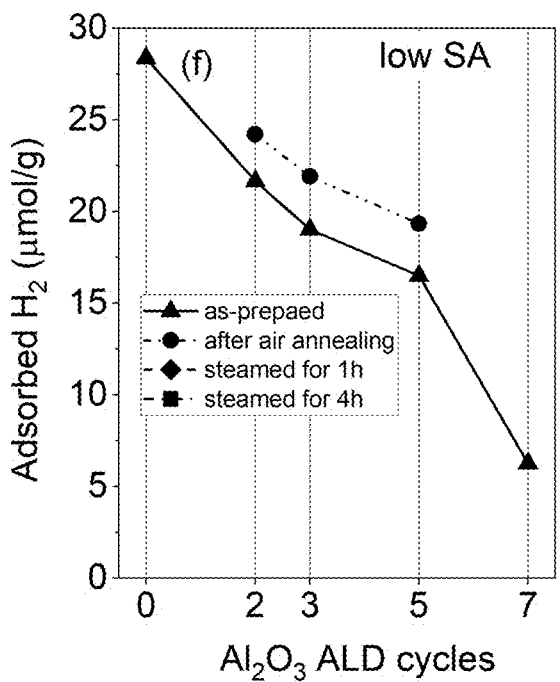

The $N_2$ physisorption analysis was applied to investigate the surface area and porosity change after different cycles of $Al_2O_3$ ALD overcoating. As the results shown in FIG. 3, there was negligible change in total surface area and pore volume after 0.1% and 0.5% Pt impregnation, suggesting the formation of sub-nanometer Pt nanoparticles. As expected, the total surface area and pore volume decreased (only exception for total surface area of catalysts on low SA support in FIG. 3(g)) with additional number of cycles of $Al_2O_3$ ALD, showing the well-controlled layer by layer $Al_2O_3$ deposition by ALD. Here we need to point out that for catalysts on high and medium SA supports, the surface area (FIGS. 3 (c) and (e)) for the 0.5% Pt impregnated catalysts were higher than the 0.1% Pt impregnated catalysts since a different batch of $Al_2O_3$ extrudates support was used. For the catalysts on ultra-high SA supports, both 0.1% Pt and 0.5% Pt impregnated catalysts were based on the same batch of $Al_2O_3$ extrudate supports. A comparison between the 0.1% Pt and 0.5% Pt catalysts showed that the surface area (FIG. 3 (a)) and pore volume (FIG. 3 (b)) after the same number of ALD cycles were very close demonstrating the excellent repeatability for the ALD overcoating process. For catalysts on low SA support, there was no surface area change after $Al_2O_3$ ALD overcoating (FIG. 3 (g)). Based on the growth rate of 1.2 Å per cycle, the thickest $Al_2O_3$ layer deposited after 7 cycles of ALD is ~0.9 nm, which was not thick enough to change the surface area of the support with the largest average pore size ~16.1 nm (cf. Table 1). During the $Al_2O_3$ ALD process, the precursors TMA and $H_2O$ were sequentially dosed into the ALD chamber at 200° C. under vacuum. To exclude the possibility of Pt nanoparticles size change after ALD, STEM images were taken on catalyst 10cAlO/0.5 Pt/low SA, which was the highest possibility for Pt nanoparticles sintering. Since this catalyst had the longest time in the ALD reactor after 10 cycles of $Al_2O_3$ ALD and due to the lowest surface area (Pt catalysts on ultra-low SA supports will not be studied, cf. FIG. 5), Pt nanoparticles had the least space to get separated. The Pt particle size remained the same (0.83±0.11 nm) suggesting that the ALD overcoating does not change the particle size. Thus, it was concluded that the ALD process does not alter the Pt nanoparticles size.

Example 6

Catalysts testing condition. In general, dehydrogenation of propane is a highly endothermic reaction requiring heating to 500 to 700° C. As reported previously, due to the positive effect of decreasing coke precursor coverage, the reaction rate was accelerated by co-feeding propane with hydrogen, thus, the equilibrium conversion was calculated by HSC Chemistry based on different $C_3H_8$ to $H_2$ ratio (H.S.C. Software, Outokumpu HSC chemistry for windows, Version 5.1, AnttiRoine, 02103-ORC-T, Pori, Finland, 2002; Saerens et al., Acs Catal 2017, 7(11), 7495-750). The catalyst tested herein were synthesized as described in Example 1. The equilibrium conversion decreased with increasing $H_2$ concentration. In the disclosure herein, the reaction temperature was set to 600° C. To minimize the coke formation in evaluation of catalyst stability due to Pt nanoparticle sintering, hydrogen was co-fed with propane with $C_3H_8:H_2$ molar ratio set to 1:1. Under this condition the equilibrium conversion is 36%. The $C_3H_8$ conversion from thermal cracking decreased with the increase of the total flow rate. To minimize the effect of high thermal cracking conversion in the analysis of the catalytic performance, total flow rate was set to 260 sccm. Here the thermal cracking conversion was below 1%.

Upon annealing in flowing air at 500° C. for 1 h, nanopores were created in an ALD overcoated layer (Karwal et al., J Vac Sci Technol A 2018, 36 (1)). Following this high temperature annealing the active surface of the underlying Pt nanoparticles can be exposed allowing propane dehydrogenation to occur. IR spectra of CO chemisorption showed the broad CO band formed at a frequency of 2040-2090 $cm^{-1}$ and was assigned to linear-bonded CO on Pt. The weaker peaks at 1830 $cm^{-1}$ were assigned to bridge-bonded CO on Pt. For the catalyst 0.5 Pt/medium SA, after 5, 7, and 10 cycles of $Al_2O_3$ ALD, the intensity of the CO chemisorption peaks decreased showing that the exposed Pt atoms are being covered by the AlOx ALD. After calcination in air at 500° C. for 1 h, the CO peaks became more pronounced indicating blockage of the Pt atoms after ALD overcoating and restoration of the gas accessibility to Pt atoms after calcination.

$H_2$ chemisorption was used to further quantify the accessibility of the Pt atoms under the overcoated $Al_2O_3$ layer. As shown in FIGS. 4 (a) and (b), the amount of adsorbed $H_2$ decreases with increasing number of ALD cycles for both series of 0.1% and 0.5% Pt catalysts, showing that the Pt nanoparticles were gradually coated with $Al_2O_3$ and the amount of deposited $Al_2O_3$ can be well controlled by the ALD process. FIG. 4 (c-f) shows the chemisorbed $H_2$ amount for all the 0.5% Pt catalysts investigated after air annealing and steaming. After annealing at 500° C. in flowing air for 1 h, more Pt atoms were exposed, which was attributed to nanopore formation from the overcoated $Al_2O_3$ layer. The percentages of exposed Pt surface sites after ALD overcoating and after air annealing are listed in Table 3.

The stability for the 0.5% Pt catalysts after ALD overcoating were tested following steam treatment (1 h and 4 h at 700° C.). As can be seen in FIG. 4 (c-f), the lines with diamond and square symbols show the amount of chemisorbed $H_2$ after steaming for 1 h and 4 h, respectively. The reduction in Pt sites caused by steaming was inversely proportional to the number of $Al_2O_3$ ALD cycles. The number of surface Pt sites further decreased after 4 h steaming for non-ALD overcoated catalysts, while the number of Pt sites for the ALD overcoated catalysts were stabilized after 1 h steaming (diamond shaped symbols). The results showed that the use of $Al_2O_3$ ALD overcoating can improve the catalysts stability to preserve the surface Pt sites.

TABLE 3

The percentage of exposed Pt Surface sites after ALD overcoating and after air annealing

| Catalysts | | The % of exposed Pt surface sites | | | | | |
|---|---|---|---|---|---|---|---|
| | | 2 cycles | 3 cycles | 4 cycles | 5 cycles | 7 cycles | 10 cycles |
| 0.5% Pt/ ultra-high SA | After $Al_2O_3$ ALD | — | 43 | — | 22 | 18 | — |
| | After air annealing | — | 58 | — | 40 | 27 | — |
| 0.5% Pt/ high SA | After $Al_2O_3$ ALD | 82 | 55 | — | 29 | 27 | — |
| | After air annealing | 90 | 69 | — | 45 | 38 | — |
| 0.5% Pt/ medium SA | After $Al_2O_3$ ALD | 72 | 61 | 49 | 42 | 26 | 24 |
| | After air annealing | 83 | 74 | 63 | 60 | 38 | 34 |
| 0.5% Pt/ low SA | After $Al_2O_3$ ALD | 76 | 67 | — | 58 | 22 | — |
| | After air annealing | | | — | | | — |

Example 7

Figure 9:
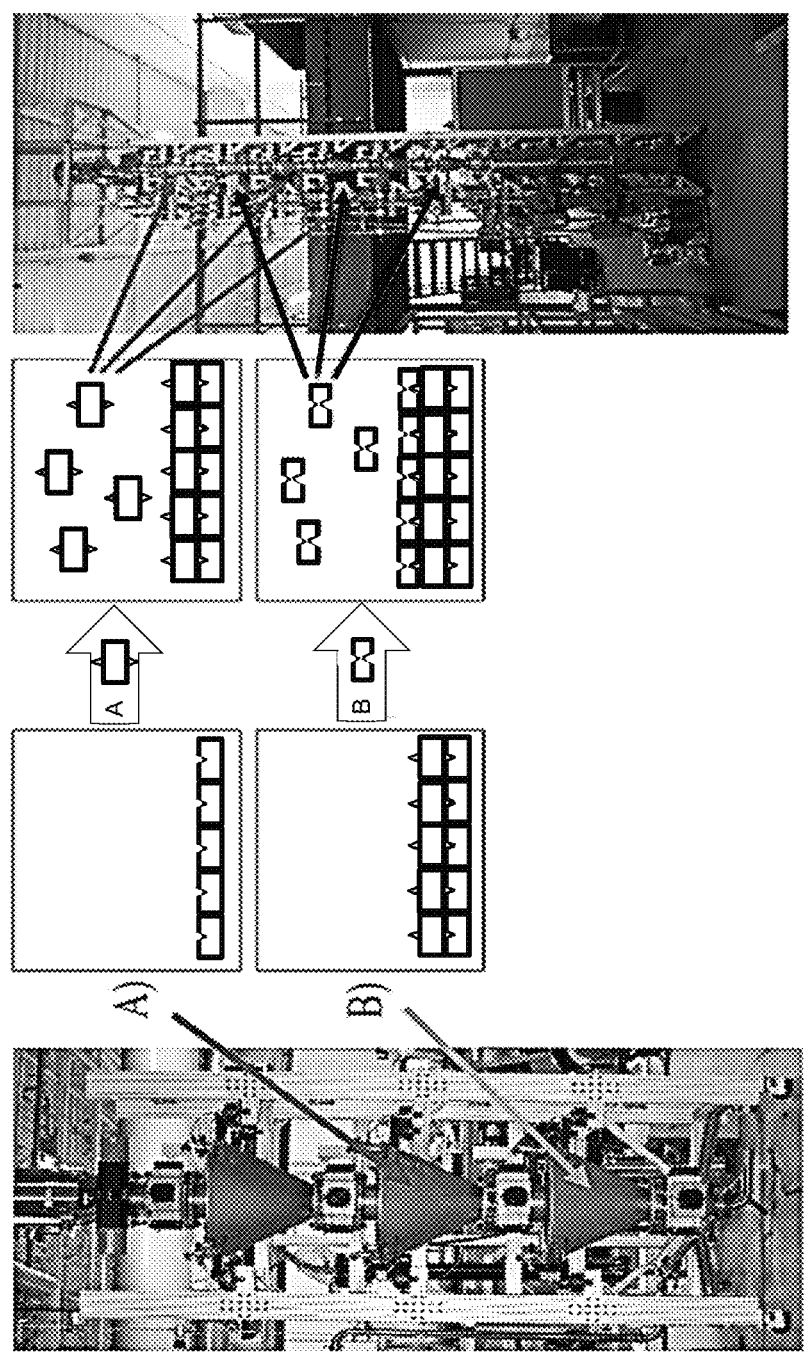
FIG. 9 shows a picture of two different ALD systems for use in methods of the disclosure. The picture on the right shows a pilot scale high throughput semi-continuous ALD system designed for 4 ALD cycles at up to 15 kg/h rates. The picture on the left shows a single cycle tower ton-scale semi-continuous ALD system for 240 kg/h rates. The schematic in the middle indicates the sequential steps of the ALD process for each system.

ALD Coating Process of the Catalyst: FIG. 9 shows images of a 4-cycle pilot-scale and 1-cycle light commercial scale ALD reactors. The ALD used was a sequential vapor-phase deposition technique. The scaling approach was to spatially segregate 'A' and 'B' precursor exposures (shown in the embedded schematic in FIG. 9) into consecutive chambers. This feature allowed the incorporation of residence time into the process sequence, which provided a substantial benefit to catalyst substrates with accessible porosity that can be coated with sufficient dwell times. Furthermore, ALD is typically operated under vacuum conditions in batch reactors, however the system used herein operated at any nominal operating pressure between rough vacuum, to higher than atmospheric pressure with minimal process impacts. This system was well-suited for either powdered catalyst materials, as well as more conventional commercial extrudates, granules or pelletized materials, and was operated with nearly 100% precursor efficiency while accommodating the substantially greater surface areas inherent to heterogeneous catalysts. The flow of powders and gases were independently controlled, and powder residence time can be modulated to balance coating efficiency and production throughput.

Residence time is a key feature of this semi-continuous production system, which provided an invaluable patent-protected process parameter. ALD was already uniquely suited for diffusion and infiltration of precursor materials into porous materials and often well outperformed solution based methods for generating similar materials. However, diffusion of the precursors and byproducts into and out of the high surface area base material was still the largest challenge. The system herein provided an ability to control residence time, which is critical to overcome the diffusion limitations encountered in such substantially high surface area powders. This also allow for quantitative control of precursor delivery and operating pressures, which maximized precursor utilization. Together the residence time, controlled delivery and pressure were used to uniquely tailor the degree of penetration of the coatings into the interior surfaces of the catalysts. The specific surface area of any powder was quantifiable using standard instrumentation techniques, and the elemental content of the metal deposited in an ALD film was measured using the Inductively Coupled Plasma Optical Emission Spectroscopy (ICP-OES), accurate to the parts per million range. Once a process was developed for the target film thickness that optimized the functional benefit of the coating, LabView software was used to execute the appropriate number of ALD "cycles" using fully-controlled exposure times. A highly-robust QA/QC plan was established simply by regularly measuring the surface area of the coated material, administering a known quantity of moles of each precursor gas into the reactor, quantifying the amount of reaction byproduct gas leaving the reactor, and measuring the ICP-OES elemental content of the amount of film material deposited on the particle surfaces.

Spatial ALD for powders was chosen because it was ideal for high volume, low ALD cycle systems, and it was envisaged here that less than ~10 ALD cycles will be required to fully stabilize the catalyst system for best-in-class durability. Each chamber carried out one ALD "half-reaction", and in the light-commercial scale system, each stack constituted one full cycle with an upper holding chamber. Powdered material (or granulates and extrudates for this application) is conveyed from chamber to chamber and stack to stack during the semi-continuous process. Thus every other chamber in the train is executed the identical process step, and all purging occurred during each conveying step (see FIG. 9). This was the embodiment of "Lean Manufacturing", as every component in the system was operating at identical throughput and there was no risk of forming bottlenecks on a production line. Additionally, the production rate was modular and easily controlled, as a loss-in-weight feeder conveyed a desired amount of material into the starting chamber, and programmable software that individually regulated the exact amount of precursor delivered to each chamber can be dialed up or down based on the current production rate; alternatively, pressures and residence times were used to vary production rates. These features enabled the installed capital cost to be minimized.

Alumina extrudates were loaded into an ALD reactor and heated to 300° C. under vacuum to remove adventitious moisture from the system. After two hours, the reactor was cooled to 200° C. for the ALD process. Nitrogen was flowed through the reactor for the duration of the experiment to act as a carrier gas for the reaction. Trimethylaluminum and water were used as precursors to form an aluminum oxide ALD overcoat, with methane forming as the reaction by-product. Different numbers of TMA and water "cycles", the process of dosing each precursor once to form a monolayer film, were completed to form aluminum oxide layers of varying thickness on the catalyst impregnated alumina extrudates. The reactor was then cooled to room temperature and unloaded. ALD coated extrudates were stored in dry boxes to limit moisture uptake during storage.

The use of the "a" or "an" are employed to describe elements and components of the embodiments herein. This is done merely for convenience and to give a general sense of the description. This description should be read to include one or at least one and the singular also includes the plural unless it is obvious that it is meant otherwise.

Still further, the figures depict embodiments for purposes of illustration only. One of ordinary skill in the art will readily recognize from the following discussion that alternative embodiments of the structures and methods illustrated herein may be employed without departing from the principles described herein.

Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed:

1. A method of manufacturing an alkane dehydrogenation catalyst comprising a catalyst support, catalytic nanoparticles, and an overcoat, the method comprising:
   calcining the catalyst support at a temperature in a range of about 500° C. to about 1200° C., wherein after calcining, the calcined catalyst support has a total surface area of 50 $m^2$/g to 350 $m^2$/g; and
   immersing the calcined catalyst support in a nanoparticle precursor solution comprising a nanoparticle precursor, under conditions sufficient to impregnate the calcined catalyst support with the nanoparticle precursor and form an impregnated catalyst precursor;
   calcining the impregnated catalyst precursor under conditions sufficient to convert the nanoparticle precursor impregnated in the impregnated catalyst precursor to catalytic nanoparticles to form a calcined impregnated catalyst precursor, wherein the calcining is done at a temperature in a range of about 150° C. to about 600° C.;
   depositing by atomic layer deposition (ALD) the overcoat onto the calcined catalyst precursor by contacting the calcined catalyst precursor with an ALD precursor and water at a temperature in a range of about 150° C. to about 300° C., and repeating the depositing step one or more times, thereby forming a catalyst intermediate;
   annealing the catalyst intermediate in air at a temperature of less than about 600° C. for about 30 minutes to about 2 hours, thereby forming the alkane dehydrogenation catalyst.

2. The method of claim 1, further comprising determining a percentage of active catalytic sites using the Chemisorption Test Method after repeating the depositing step at least one time and further repeating the depositing step if the percentage of active catalytic sites is greater than or equal to 50%.

3. The method of claim 1, wherein the catalyst support comprises $Al_2O_3$.

4. The method of claim 1, wherein the catalyst support is an extrudate.

5. The method of claim 1, wherein the catalyst support is calcined at a temperature in the range of about 500° C. to about 1050° C.

6. The method of claim 1, wherein the catalyst support has a pore volume of 0.8 cm$^3$/g to 0.4 cm$^3$/g, and an average pore size of 3 nm to 20 nm as determined by Hg porosimetry.

7. The method of claim 1, wherein the nanoparticle precursor comprises one or more of $H_2PtCl_6$, chloroplatinic acid, ammonium chloroplatinate, bromoplatinic acid, platinum trichloride, platinum tetrachloride hydrate, platinum dichlorocarbonyl dichloride, tetraamineplatinum chloride, dinitrodiaminoplatinum, and sodium tetranitroplatinate (II).

8. The method of claim 1, wherein the nanoparticle precursor is present in the nanoparticle precursor solution at a concentration of about 0.1 M to about 3 M.

9. The method of claim 1, wherein the calcined catalyst support has a total surface area of about 70 m$^2$/g to about 300 m$^2$/g.

10. The method of claim 1, wherein the ALD precursor comprises one or more of Al, Ti, Nb, Zr, and V.

11. The method of claim 10, wherein the ALD precursor comprises one or more of $Al(CH_3)_3$, $TiCl_4$, $ZrCl_4$, $Zr(N(CH_3)_2)_4$, $Nb(OCH_2CH_3)_5$, and $V(O)(OCH(CH_3)_2)_3$.

12. The method of claim 1, wherein the depositing step is repeated 2 to 8 times.

13. The method of claim 1, wherein depositing the overcoat onto the calcined catalyst precursor occurs at a temperature of about 200° C. and/or the overcoat is deposited onto the calcined catalyst precursor under vacuum.

14. The method claim 1, wherein the ALD overcoat covers approximately 10% to 60% of the total surface area of the catalytic nanoparticles.

* * * * *